(12) United States Patent
Little et al.

(10) Patent No.: US 11,020,028 B2
(45) Date of Patent: *Jun. 1, 2021

(54) FOLDOVER SENSORS AND METHODS FOR MAKING AND USING THEM

(71) Applicant: Medtronic MiniMed, Inc., Northridge, CA (US)

(72) Inventors: Megan E. Little, Claremont, CA (US); Katherine T. Wolfe, Dunwoody, GA (US); Raghavendhar Gautham, Los Angeles, CA (US); Bradley C. Liang, Bloomfield Hills, MI (US); Rajiv Shah, Rancho Palos Verdes, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/216,838

(22) Filed: Dec. 11, 2018

(65) Prior Publication Data
US 2020/0077930 A1 Mar. 12, 2020

Related U.S. Application Data

(63) Continuation of application No. 15/272,225, filed on Sep. 21, 2016, now Pat. No. 10,188,326, which is a (Continued)

(51) Int. Cl.
*A61B 5/145* (2006.01)
*A61B 5/1486* (2006.01)
(Continued)

(52) U.S. Cl.
CPC ...... *A61B 5/14532* (2013.01); *A61B 5/14865* (2013.01); *C12Q 1/001* (2013.01);
(Continued)

(58) Field of Classification Search
CPC ... C12Q 1/00; C12Q 1/02; C12Q 1/34; C12Q 1/54; G01N 27/327; G01N 27/3272; A61B 5/150274; B32B 38/04
See application file for complete search history.

(56) References Cited

U.S. PATENT DOCUMENTS 4,431,004 A 2/1984 Bessman et al.
4,562,751 A 1/1986 Nason et al.
(Continued)

FOREIGN PATENT DOCUMENTS

CN 101052727 10/2007
CN 103269641 8/2013
(Continued)

OTHER PUBLICATIONS

Canadian Office Action dated Feb. 13, 2019, application No. 2,870,481.
(Continued)

*Primary Examiner* — Gurpreet Kaur
(74) *Attorney, Agent, or Firm* — Gates & Cooper LLP

(57) ABSTRACT

The invention disclosed herein includes sensors having three dimensional configurations that allow expansive "360°" sensing (i.e. sensing analyte from multiple directions) in the environments in which such sensors are disposed. Embodiments of the invention provide analyte sensors having foldable substrates adapted to produce optimized configurations of electrode elements as well as methods for making and using such sensors. Typical embodiments of the invention include glucose sensors used in the management of diabetes.

16 Claims, 19 Drawing Sheets

Related U.S. Application Data continuation of application No. 13/779,271, filed on Feb. 27, 2013, now Pat. No. 9,493,807.

(60) Provisional application No. 61/651,889, filed on May 25, 2012.

(51) Int. Cl.
  *G01N 27/327* (2006.01)
  *C12Q 1/00* (2006.01)

(52) U.S. Cl.
  CPC .......... *C12Q 1/006* (2013.01); *G01N 27/3272* (2013.01); *A61B 2562/125* (2013.01); *A61B 2562/166* (2013.01); *A61B 2562/222* (2013.01); *Y10T 29/49204* (2015.01)

(56) References Cited

U.S. PATENT DOCUMENTS

| | | |
|---|---|---|
| 4,573,994 A | 3/1986 | Fischell et al. |
| 4,678,408 A | 7/1987 | Nason et al. |
| 4,685,903 A | 8/1987 | Cable et al. |
| 4,703,756 A | 11/1987 | Gough et al. |
| 4,755,173 A | 7/1988 | Konopka et al. |
| 5,299,571 A | 4/1994 | Mastrototaro |
| 5,390,691 A | 2/1995 | Sproule et al. |
| 5,391,250 A | 2/1995 | Cheney, II et al. |
| 5,482,473 A | 1/1996 | Lord et al. |
| 5,485,408 A | 1/1996 | Blomquist |
| 5,494,562 A | 2/1996 | Maley et al. |
| 5,522,803 A | 6/1996 | Teissen-Simony |
| 5,568,806 A | 10/1996 | Cheney, II et al. |
| 5,605,152 A | 2/1997 | Slate et al. |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 5,985,129 A | 11/1999 | Gough et al. |
| 6,001,067 A | 12/1999 | Shults et al. |
| 6,017,328 A | 1/2000 | Fischell et al. |
| 6,119,028 A | 9/2000 | Schulman et al. |
| 6,120,676 A | 9/2000 | Heller et al. |
| 6,122,536 A | 9/2000 | Sun et al. |
| 6,141,573 A | 10/2000 | Kurnik et al. |
| 6,186,982 B1 | 2/2001 | Gross et al. |
| 6,212,416 B1 | 4/2001 | Ward et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,400,974 B1 | 6/2002 | Lesho |
| 6,484,045 B1 | 11/2002 | Holker et al. |
| 6,512,939 B1 | 1/2003 | Colvin et al. |
| 6,514,718 B2 | 2/2003 | Heller et al. |
| 6,542,765 B1 | 4/2003 | Guy et al. |
| 6,544,212 B2 | 4/2003 | Galley et al. |
| 6,558,351 B1 | 5/2003 | Steil et al. |
| 6,515,919 B1 | 7/2003 | Berner et al. |
| 6,591,876 B2 | 7/2003 | Safabash |
| 6,641,533 B2 | 11/2003 | Causey, III et al. |
| 6,702,857 B2 | 3/2004 | Brauker et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,033,336 B2 | 4/2006 | Hogendijk et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,493,807 B2 | 11/2016 | Little et al. |
| 10,188,326 B2 * | 1/2019 | Little .................. C12Q 1/001 |
| 2004/0025238 A1 | 2/2004 | Parsons et al. |
| 2005/0008671 A1 | 1/2005 | Van Antwerp et al. |
| 2005/0115832 A1 | 6/2005 | Simpson et al. |
| 2007/0123819 A1 | 5/2007 | Mernoe et al. |
| 2007/0163894 A1 | 7/2007 | Wang et al. |
| 2007/0227907 A1 | 10/2007 | Shah et al. |
| 2007/0235337 A1 | 10/2007 | Simpson et al. |
| 2010/0025238 A1 | 2/2010 | Gottlieb et al. |
| 2010/0160861 A1 | 6/2010 | Causey, III et al. |
| 2011/0152654 A1 | 6/2011 | Wang et al. |
| 2011/0230735 A1 * | 9/2011 | Wolfe ................ A61B 5/14503 600/309 |
| 2011/0297555 A1 | 12/2011 | Stien et al. |
| 2011/0319734 A1 | 12/2011 | Gottlieb et al. |
| 2013/0240375 A1 | 9/2013 | Blythe et al. |

FOREIGN PATENT DOCUMENTS

| | | |
|---|---|---|
| EP | 1153571 | 11/2001 |
| EP | 1909098 | 4/2008 |
| JP | 2000-065777 | 3/2000 |
| JP | 2006-184270 | 7/2006 |
| JP | 2009-544407 | 12/2009 |
| WO | 2001058348 | 8/2001 |
| WO | 2003022128 | 3/2003 |
| WO | 2003022352 | 3/2003 |
| WO | 2003023388 | 3/2003 |
| WO | 2003023708 | 3/2003 |
| WO | 2003034902 | 5/2003 |

(56) References Cited

FOREIGN PATENT DOCUMENTS

| WO | 2003035117 | 5/2003 |
|----|------------|--------|
| WO | 2003035891 | 5/2003 |
| WO | 2003036255 | 5/2003 |
| WO | 2003036310 | 5/2003 |
| WO | 2003074107 | 9/2003 |
| WO | 2004021877 | 11/2006 |
| WO | 2008042625 | 4/2008 |
| WO | 2011/063259 | 5/2011 |
| WO | 2011/064780 | 6/2011 |
| WO | 2011163303 | 12/2011 |
| WO | 2013177573 | 11/2013 |

OTHER PUBLICATIONS

Japanese Office Action (with English translation) from Japanese Patent Application No. 2015-514238 dated Dec. 1, 2015.
Chinese Office Action (with English translation) from Chinese Patent Application No. 201380023885.0 dated Feb. 1, 2016.

* cited by examiner (b) tubeless assembly (a) tubed assembly

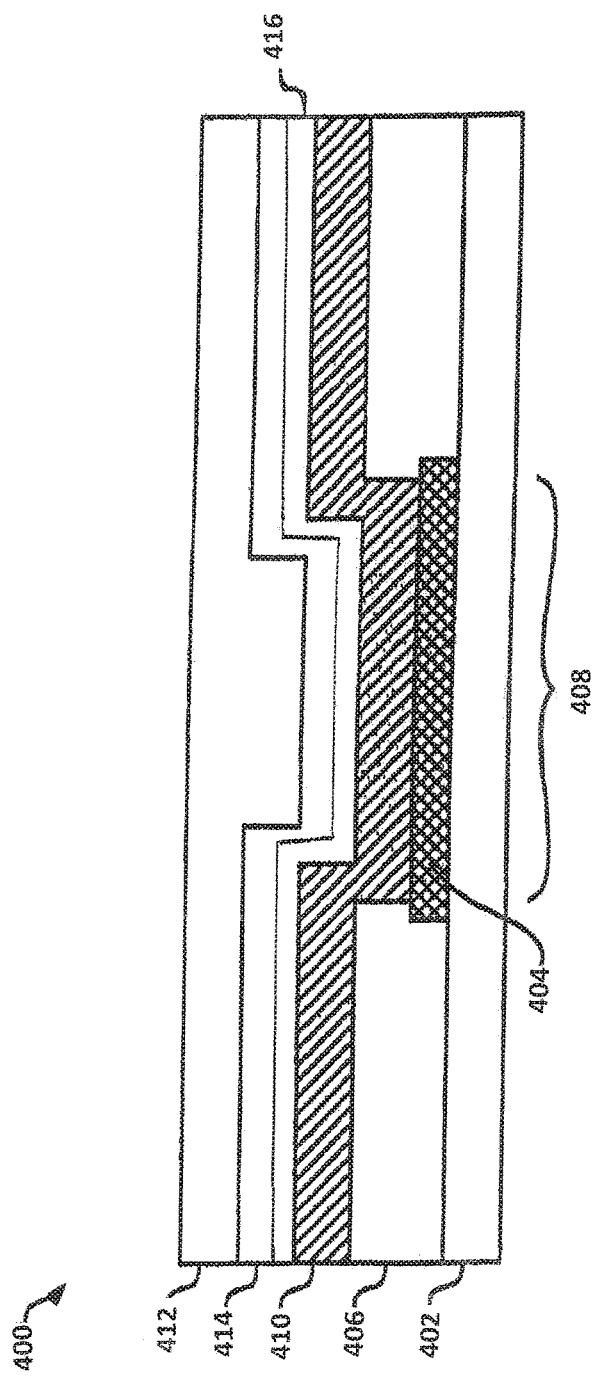

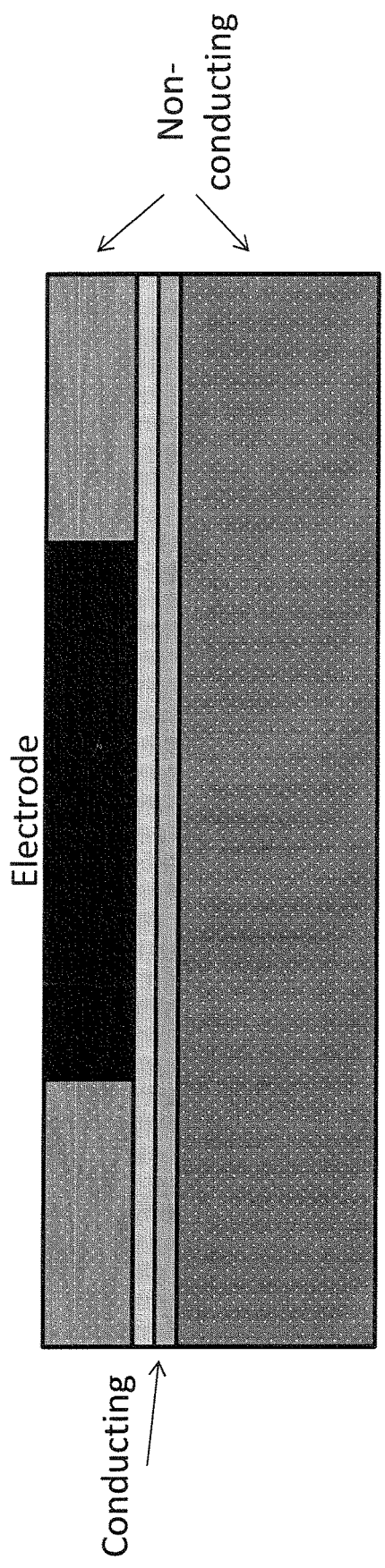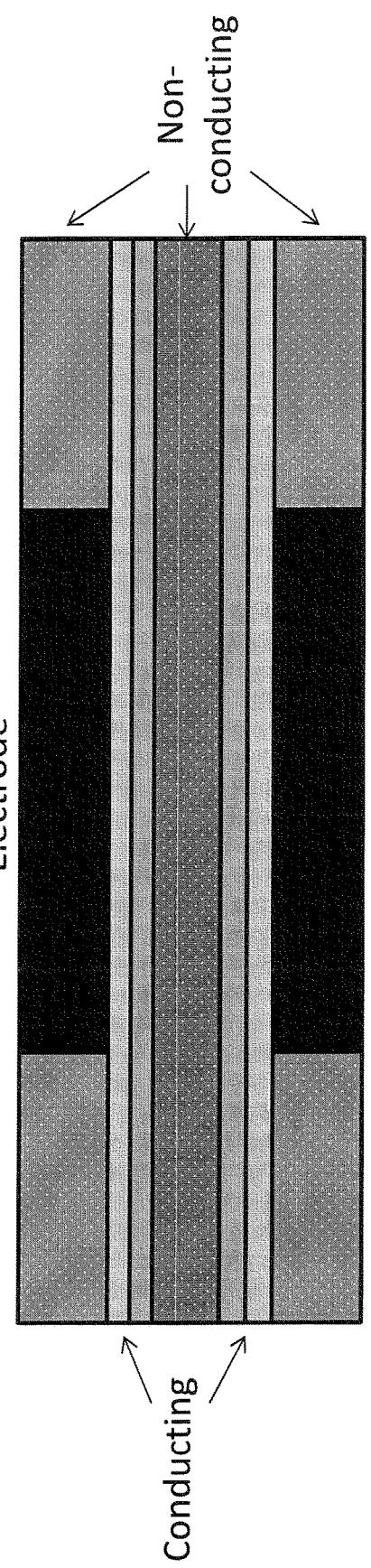
FIG. 12B Single-sided Sensor
FIG. 12C Double-sided Sensor

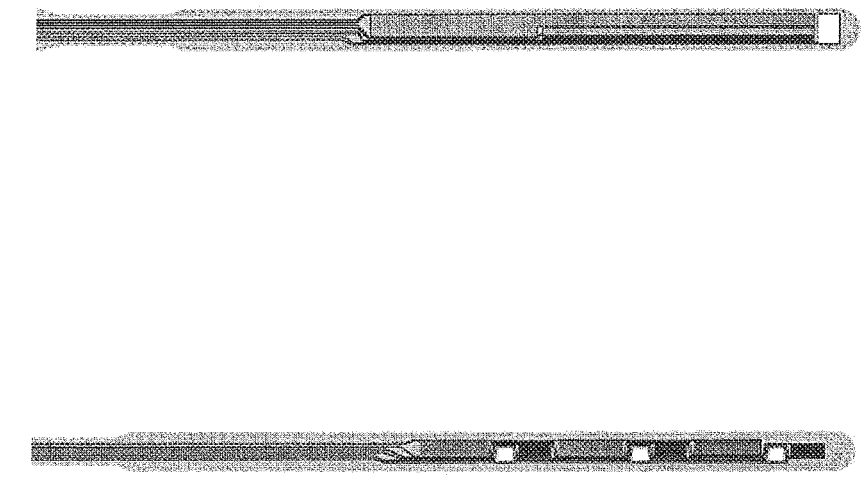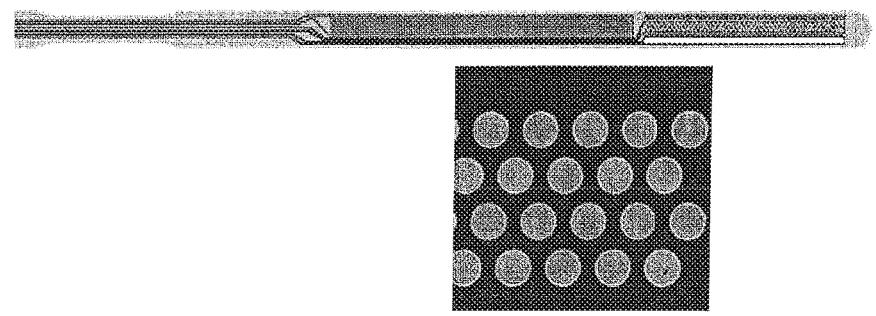
FIG. 13A1 Rectangular "Traditional"
FIG. 13A2 MicroArray
FIG. 13B1 Distributed
FIG. 13B2 Micro-Parallel
Electrode Types

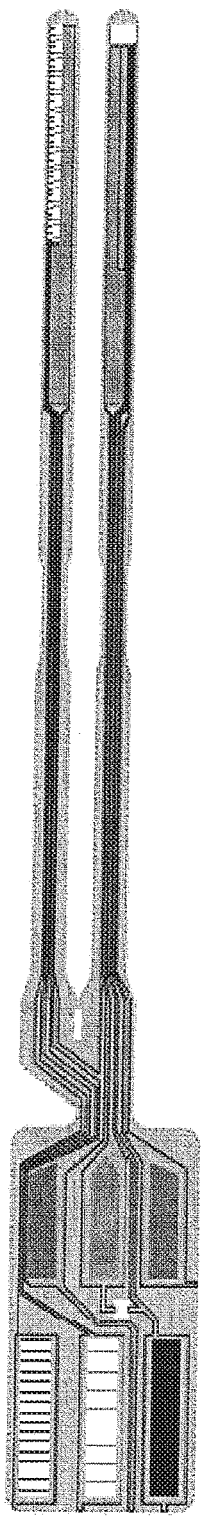
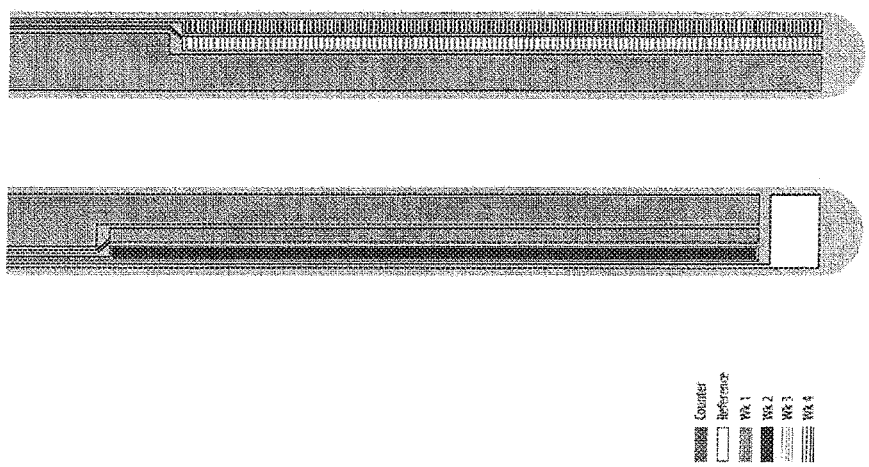
FIG. 13C1
6-Pin Ferrari Designs (4 independent WE)
FIG. 13C2  FIG. 13C3

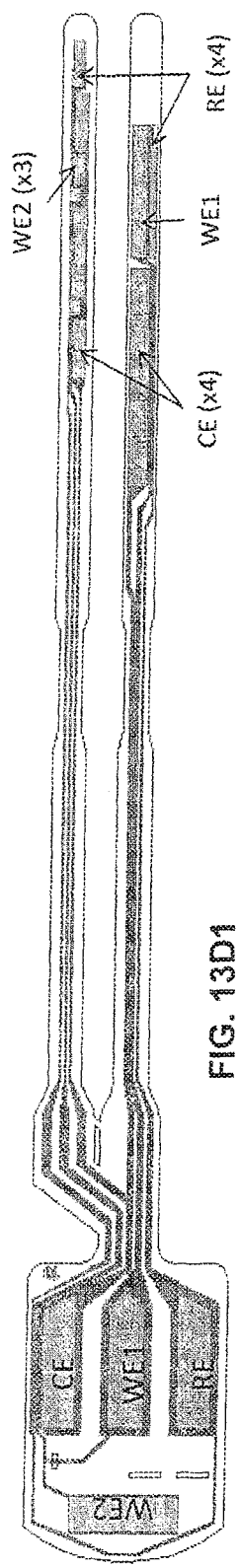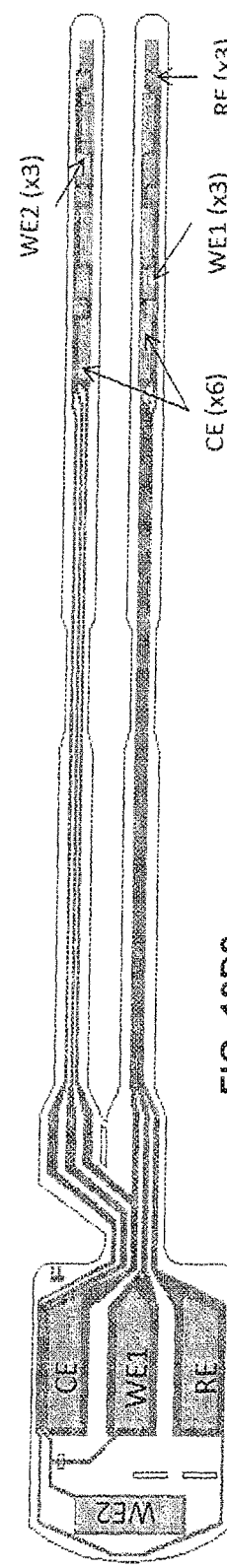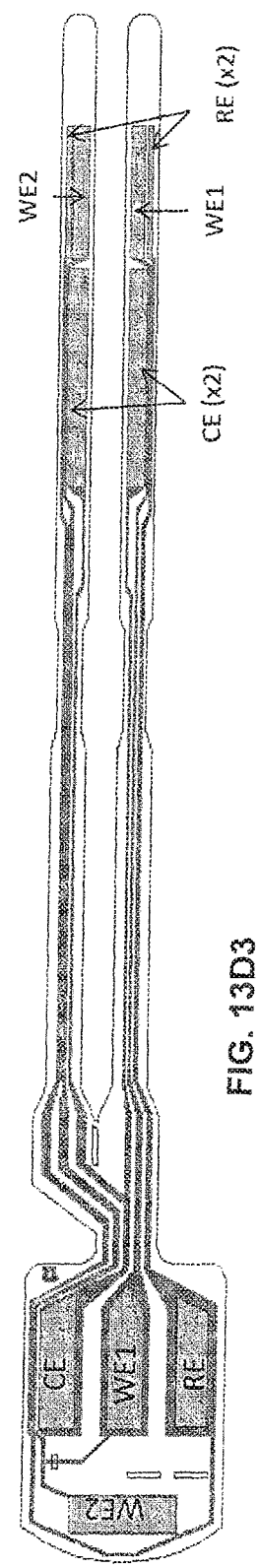
FIG. 13D1  FIG. 13D2  FIG. 13D3

FOLDOVER SENSORS AND METHODS FOR MAKING AND USING THEM

CROSS REFERENCE TO RELATED APPLICATIONS

This application is a continuation application that claims the benefit under 35 U.S.C. 120 of U.S. patent application Ser. No. 15/272,225, filed Sep. 21, 2016, which is a continuation application that claims the benefit under 35 U.S.C. 120 of U.S. patent application Ser. No. 13/779,271, filed Feb. 27, 2013, which claims priority under Section 119(e) from U.S. Provisional Application Ser. No. 61/651,889, filed May 25, 2012, the contents of which are incorporated herein by reference.

TECHNICAL FIELD

The invention relates to analyte sensors such as glucose sensors useful in the management of diabetes.

BACKGROUND OF THE INVENTION

Electrochemical sensors are commonly used to detect or measure the concentrations of in vivo analytes, such as glucose. Typically in such analyte sensing systems, an analyte (or a species derived from it) is electro-active and generates a detectable signal at an electrode in the sensor. This signal is then correlated with the presence or concentration of the analyte within a biological sample. In some conventional sensors, an enzyme is provided that reacts with the analyte to be measured, the byproduct of the reaction being qualified or quantified at the electrode. In one conventional glucose sensor, immobilized glucose oxidase catalyzes the oxidation of glucose to form hydrogen peroxide, which is then quantified by amperometric measurements (e.g. change in electrical current) through one or more electrodes.

In order to reduce the size of the sensors and/or increase their sensitivity and efficiency, electrochemical sensors can be patterned with multiple electrodes on both sides of the sensor. A variety of electrochemical sensors have also been developed to be multi-layered (e.g. double-sided), comprising multiple layers of electrodes and conductors interposed between multiple layers of dielectric materials. The electrochemical properties of multilayered sensors can be tailored by altering certain design parameters (e.g. number of internal layers, layer thickness, area under the electrodes). However, fabricating such sensors requires extra steps such as the patterning both/multiple sides of sensor elements. Consequently, fabricating such multilayer sensors requires complicated and costly processes including, for example, reiteratively layering multiple elements. In addition, multilayer sensors typically require the use of vias (vertical interception access) to establish vertical electrical connections between the different layers of conductors, elements which add to the cost and complexity of fabricating such sensors.

There is a need for cost-effective sensors that provide the size, sensitivity, and efficiency advantages of double-sided and multilayer sensors, as well as simplified manufacturing processes for fabricating such sensors.

SUMMARY OF THE INVENTION

The invention disclosed herein includes sensors having three dimensional configurations that allow expansive "360°" sensing (i.e. sensing analyte from multiple directions) in the environments in which such sensors are disposed. As discussed in detail below, sensors that provide such expansive sensing have advantages over sensors that obtain information from a single location within a sensing environment. Embodiments of the invention include amperometric analyte sensors formed from a foldable base substrate as well as amperometric analyte sensors formed from multiple base substrates that are adhered together. Such sensor designs provide a number of advantageous characteristics in certain contexts, for example by facilitating sensor production processes as well as analyte detection and/or characterization.

The invention disclosed herein has a number of embodiments. An illustrative embodiment of the invention is an analyte sensor apparatus comprising a base substrate comprising planar sheet of a flexible material adapted to transition from a first configuration to a second configuration when the base substrate is folded to form a fixed bend. In such embodiments of the invention, a working electrode, a counter electrode and a reference electrode are disposed upon a first surface of the base substrate which is then folded to introduce fixed bends that produce specific sensor electrode configurations, for example, an electrode configuration where at least one electrode is disposed on a first side of the fixed bend; and at least one electrode is disposed on a second side of the fixed bend. Typically, other electronic elements are disposed on the first surface of the base substrate, such as a plurality of contact pads and/or as a plurality of electrical conduits adapted to transmit electrical signals between electrodes and contact pads.

As discussed in detail below, the base substrate can be made from a variety of materials and formed into a wide variety of shapes. In illustrative working embodiments of the invention that are disclosed herein, the base substrate material can include a polymeric composition such as a polyimide. In one working embodiment of the invention that is shown in FIG. 1, the base substrate is formed into a shape that comprises a rectangular body, a first longitudinal arm extending outward from the rectangular body, and a second longitudinal arm extending outward from the rectangular body. In this illustrative working embodiment, the first longitudinal arm and the second longitudinal arm are parallel to each other. In certain embodiments of the invention, additional elements are used to facilitate base substrate manipulation and/or to stabilize a manipulated base architecture. Optionally for example, a base substrate comprises a mark or other feature located in an area at which the base is folded in order to facilitate folding, for example a demarcation, a perforation, or a kiss cut. In some embodiments of the invention, the sensor apparatus comprises a locking member that is adapted to inhibit movement of one or more elements that form or are coupled to the folded base substrate (e.g. to inhibit movement of the first longitudinal arm or the second longitudinal arm). In some embodiments of the invention, the sensor apparatus comprises a spacing member that is adapted to maintain a minimal distance between one or more elements of the folded base substrate (e.g. the first longitudinal arm and the second longitudinal arm).

In typical embodiments of the invention, the sensor apparatus comprises a plurality of working electrodes, for example, a first working electrode disposed on the first longitudinal arm and a second working electrode disposed on the second longitudinal arm (and/or multiple working electrodes disposed on one or both longitudinal arm(s)). In some embodiments of the invention, the base substrate comprises a plurality of reference electrodes, a plurality of working electrodes and a plurality of counter electrodes clustered together in units consisting essentially of one working electrode, one counter electrode and one reference electrode. Typically such clustered units are longitudinally distributed on the base substrate in a repeating pattern of units. In typical embodiments of the invention, the fixed bend in the base substrate configures the substrate in an architecture that results in at least one electrode located on the first side of the fixed bend and at least one electrode located on the second side of the fixed bend facing opposite directions.

Embodiments of the invention can include other structural elements designed for use in specific analyte environments. For example, in some embodiments, the sensor is disposed within a housing (e.g. a tube) and adapted to be implanted in vivo (e.g. the tubed assembly embodiment shown in FIG. 6A). Typically, in such embodiments, the housing comprises an aperture adapted to allow an aqueous medium in which the apparatus is disposed to contact a working electrode. In alternative embodiments of the invention the apparatus does not comprise a housing that surrounds the sensor (e.g. the tubeless assembly shown in FIG. 6B). In these embodiments, the sensor is disposed within a needle adapted to pierce a tissue and implant the apparatus in vivo. Typically, in such embodiments, the needle is adapted to be removed from the tissue following implantation of the analyte sensor apparatus.

Embodiments of the invention include further elements designed for use with the folded sensors that are disclosed herein, for example those that are designed to analyze electrical signal data obtained from electrodes disposed on the folded base substrate. In some embodiments of the invention, the analyte sensor apparatus includes a processor and a computer-readable program code having instructions, which when executed, cause the processor to assess electrochemical signal data obtained from at least one working electrode and then compute analyte concentrations based upon the electrochemical signal data obtained from the working electrode. In certain embodiments of the invention, the processor compares electrochemical signal data obtained from multiple working electrodes in order to, for example, adapt different electrodes to sense different analytes, and/or to focus on different concentration ranges of a single analyte; and/or to identify or characterize spurious sensor signals (e.g. sensor noise, signals caused by interfering compounds and the like) so as to enhance the accuracy of the sensor readings.

A related embodiment of the invention is a method of making a folded analyte sensor apparatus that is disclosed herein. Typically, such methods include the initial steps of providing a base substrate formed from a planar sheet of a flexible material having a first surface and a second surface and adapted to transition from a first configuration to a second configuration when the base substrate is folded. In the working embodiments of the invention that are disclosed herein, the base substrate is designed to include a rectangular body, a first longitudinal arm extending outward from the rectangular body; and a second longitudinal arm extending outward from the rectangular body. Typical embodiments of the invention include forming a plurality of contact pads and a plurality of electrical conduits upon the first surface of the base substrate. In such embodiments of the invention, the plurality of electrical conduits are of a size and formed from material that allows them to transmit electrical signals between electrodes and contact pads separated by the fixed bend. These methods also include the steps of forming a working electrode, a counter electrode and a reference electrode on the first surface of the base substrate. Typically, at least one of these electrodes is formed on the first longitudinal arm and at least one other electrode is formed on the second longitudinal arm of the base substrate. These methods further include adding layers of materials onto one or more electrodes, for example, forming an analyte sensing layer on the working electrode that detectably alters the electrical current at the working electrode in the presence of an analyte as well as forming an analyte modulating layer on the analyte sensing layer that modulates the diffusion of analyte therethrough. In certain embodiments of the invention, the analyte sensing layer comprises glucose oxidase. Optionally, the analyte modulating layer comprises a hydrophilic polymer, for example a linear polyurethane/polyurea polymer and/or a branched acrylate polymer.

Methods for making sensor embodiments of the invention include folding the base substrate so as to introduce a fixed bend that results in a configuration where at least one electrode is disposed on a first side of the fixed bend, and at least one electrode is disposed on a second side of the fixed bend. In this way, a folded analyte sensor embodiment of the invention can be formed. These methods can be used to produce a wide variety of the folded sensor structures. For example, in some embodiments of the invention, the base substrate is formed so that the first longitudinal arm and the second longitudinal arm are parallel to each other. Optionally in such embodiments, the base substrate is folded so that the first longitudinal arm and the second longitudinal arm are superimposed on each other. In certain embodiments of the invention, the base substrate is folded to introduce a fixed bend that configures the substrate in an orientation so that at least one electrode on the first side of the fixed bend and at least one electrode on the second side of the fixed bend face opposite directions. In other embodiments of the invention, the base substrate is folded so that the first side of the base substrate that results from the fixed bend is in a plane is at least 45 or 90 degrees off of the second side of the substrate that results from the fixed bend.

Embodiments of the invention are adapted for use with a variety of electrode configurations. For example, in some embodiments of the invention, the sensor includes a single working electrode, counter electrode and reference electrode formed on the base substrate. In other embodiments of the invention, a plurality of working electrodes, counter electrodes and reference electrodes clustered together in units consisting essentially of one working electrode, one counter electrode and one reference electrode are formed on the base substrate, and the clustered units are longitudinally distributed on at least one longitudinal arm of the base substrate in a repeating pattern of units. In certain embodiments of the invention, one or more electrodes is formed an array of electrically conductive members disposed on the base substrate, the electrically conductive members are circular and have a diameter between 10 µm and 400 µm; and the array comprises at least 10 electrically conductive members.

Yet another embodiment of the invention is a method of sensing an analyte within the body of a mammal. Typically, this method comprises implanting an analyte sensor having a folded architecture within the mammal (e.g. in the interstitial space of a diabetic individual), sensing an alteration in current at the working electrode in the presence of the analyte; and then correlating the alteration in current with the presence of the analyte, so that the analyte is sensed. While typical embodiments of the invention pertain to glucose sensors, the folded sensor designs disclosed herein can be adapted for use with a wide variety of devices known in the art.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 26 in U.S. Pat. No. 6,484,045). As shown in this figure, the base matrix has a shape that includes a rectangular body (500); a first longitudinal arm extending outward from the rectangular body (520); and a second longitudinal arm (530) extending outward from the rectangular body. In this embodiment, the rectangular body and the longitudinal arms are linked by a neck region (510).

FIGS. 2A-2C illustrate one embodiment of a foldover sensor. FIG. 2(a) shows the sensor prior to folding, FIG. 2(b) shows the front surface of the foldover sensor after folding, and FIG. 2(c) shows the back surface of the foldover sensor after folding.

FIGS. 3A-3D illustrate one embodiment of a sensor and graphed sensor data. FIG. 3(a) shows a top-down view of a foldover sensor prior to folding over a longitudinal axis represented by a dotted line and FIG. 3(b) shows a side view of the foldover sensor with the electrodes (black) facing out after folding. FIGS. 3C and 3D provide data from studies of such sensor structures in a In Vitro Testing System (BTS) that is designed to mimic in vivo conditions. In this system, sensor current is measured periodically in the presence of known concentrations of glucose and glucose values are then correlated with Isig, that is sensor current (in nA). These graphs provide data (Isig over periods of time) from experiments using sensors constructed to include in FIG. 3(C): tubed sensors with the electrodes facing out and in FIG. 3(D) tubeless sensors with the electrodes facing out. In this system, sensor current is measured periodically (typically once every five minutes) in the presence of known concentrations of glucose and glucose values are then correlated with ISIG, that is sensor current (in nA). When used in in vivo environments such as an interstitial space, these sensors can be used to measure glucose using calculations based on a formula IG=ISIG×CAL, where IG is interstitial glucose value (in mmol/l or mg/dl), ISIG is sensor current (in nA) and CAL is calibration factor (in mmol/l/µA or mg/dl/µA).

FIG. 8(b) showing a complimentary flap in the other longitudinal member; and FIG. 8(c) showing an embodiment showing a spacer disposed on and/or between the first longitudinal arm and the second longitudinal arm.

As shown in FIG. 11, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (Isig) that is output from the potentiostat.

FIGS. 12A-C show illustrations of amperometric analyte sensors formed from a plurality of planar layered elements. FIG. 12A shows an illustration of an electrode coated with various material layers. FIG. 12B shows an illustration of a single sided sensor embodiment. FIG. 12C shows an illustration of a double sided sensor embodiment. The substrate design consists of the following layers in the embodiments shown in FIGS. 12B and 12C: a base polyimide (non-conducting) layer; a metallization layer patterned to form desired electronic elements; and an insulation polyimide (non-conducting) layer, patterned to form electrode and contact pad designs.

FIG. 13A-13D show illustrations of a number of different electrode and electronic element configurations useful with embodiments of the invention. FIG. 13A1 shows a rectangular "traditional" electrode configuration; FIG. 13A2 shows a microarray electrode configuration (with magnification of the microarray on left); FIG. 13B1 shows a distributed electrode configuration; FIG. 13B2 shows a micro-parallel electrode configuration; FIG. 13C1 shows a 6-pin electrode design; FIG. 13C2 shows a close up view of electrode arrangements in the lower longitudinal arm of the embodiment shown in FIG. 13C1; FIG. 13C3 shows a close up view of electrode arrangements in the upper longitudinal arm of the embodiment shown in FIG. 13C1; and FIG. 13D1 shows a first illustrative configuration of electrodes; FIG. 13D2 shows a second illustrative configuration of electrodes; and FIG. 13D3 shows a third illustrative configuration of electrodes useful with embodiments of the invention.

DETAILED DESCRIPTION OF THE INVENTION

Figure 1:
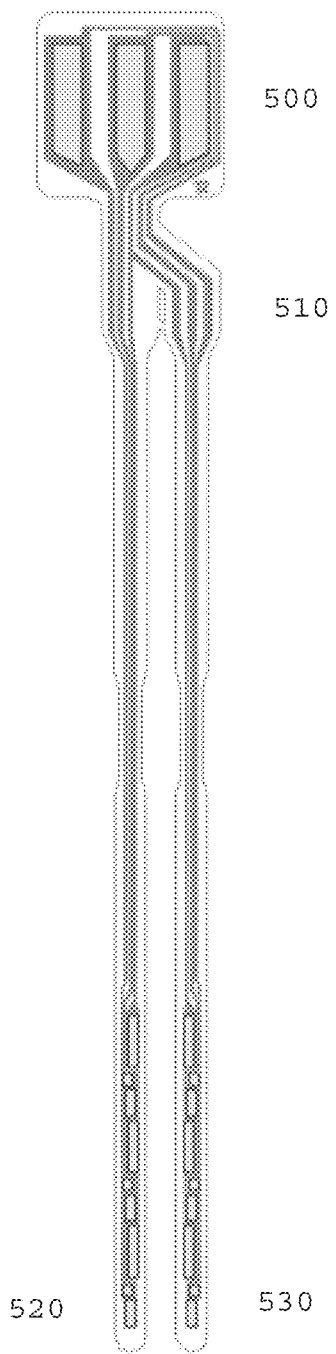
FIG. 1 is a top-down view illustrating one embodiment of a front surface of a foldover sensor having a first longitudinal member and a second longitudinal member each of which includes a three grouped units of working, counter and reference electrodes that are operably connected to a distal connection elements(s) by traces (for a comparison of this embodiment to conventional, non-folded structures, see, e.g.

Unless otherwise defined, all terms of art, notations, and other scientific terms or terminology used herein are intended to have the meanings commonly understood by those of skill in the art to which this invention pertains. In some cases, terms with commonly understood meanings may be defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All numbers recited in the specification and associated claims that refer to values that can be numerically characterized with a value other than a whole number (e.g. a distance) are understood to be modified by the term "about". Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Furthermore, all publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

As discussed in detail below, embodiments of the invention relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors elements, including for example, those disclosed in U.S. Patent Application Nos. 20050115832, 20050008671, 20070227907, 20400025238, 20110319734, 20110152654 and Ser. No. 13/707,400 filed Dec. 6, 2012, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391,250, 5,482,473, 5,299,571, 5,568,806, 5,494,562, 6,120,676, 6,542,765, 7,033,336 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO 03/036310 WO 08/042, 625, and WO 03/074107, and European Patent Application EP 1153571, the contents of each of which are incorporated herein by reference.

A. Illustrative Embodiments of the Invention and Associated Characteristics

Illustrative Embodiments

The invention disclosed herein includes sensors having three dimensional configurations that allow expansive 360° sensing (i.e. sensing analyte from multiple directions) in the environments in which such sensors are disposed. As discussed in detail below, sensors that provide such expansive sensing have advantages over sensors that obtain information from a single location within a sensing environment. Embodiments of the invention include amperometric analyte sensors formed from a foldable base substrate as well as amperometric analyte sensors formed from multiple base substrates that are adhered together.

While the disclosure focuses primarily on embodiments of the invention that utilize foldable base substrates, those of skill in this technology understand that this disclosure is readily adapted for use with embodiments of the invention that utilize two or more base substrates (e.g. as sensor element modules) that are adhered together. Such modular double-sided sensors can be made by overlaying or otherwise combining two sensor substrates with active sensor electrodes to create a single implant sensor. Such double-sided sensors can be used to control the proximity of electrodes within an implant and/or their relative proximity to each other. Moreover, such modular double-sided sensor can be combined with the fold-over sensors disclosed herein to generate further sensor embodiments. Benefits of such modular sensors include greater mechanical stability by doubling implant thickness while simultaneously avoiding the creation of a sensor that is too thick/stiff (and therefore prone to breaking).

Embodiments of the invention disclosed herein include amperometric analyte sensors formed from a foldable base substrate. Such foldover sensor embodiments can be used as a means of putting the electrodes on the opposite side of contact/bond pads without using vias, thereby simplifying the production process and reducing associated costs. Benefits of the foldover sensor include the selective positioning of electrical elements with minimal effort. Consequently, such embodiments allow electrodes to be placed on both sides of a substrate, for example so that working and counter electrodes can be separated (e.g. so as to minimize interference from one electrode to another). Foldover sensor embodiments can also incorporate multiple working electrodes to get spatial separation between redundant electrodes that are designed to sense analytes such as glucose. In this way, such embodiments can overcome problems that can occur when a sensor electrode is disposed into a localized suboptimal in vivo environment (e.g. localized scar tissue and the like). Certain foldover sensor embodiments such as the one shown in FIG. 1 can be folded and placed into a needle that pierces a tissue in which the sensor is implanted. This allows a sensor to be inserted in vivo in a simple step. Moreover, in certain embodiment, two arms of a base substrate can then flex outward from each other to increase a separation distance in vivo. This flexing consequently increases the spatial separation of sensor electrodes so as reduce problematical issues such as those associated with localized analyte concentration changes or tissue (e.g. scar tissue) effects.

As discussed below, sensor base substrates can be folded a number of ways to generate various embodiments of the invention. For example, sensor base substrates such as the embodiment shown in FIG. 1 can be folded back on itself at the tip to make assembly easier (see, e.g. FIG. 5). Such embodiments can provide a desirable separation distance between electrodes while allowing the tips to remain joined. In other embodiments of the invention folding is used to reduce the length of a sensor that is implanted in vivo. Moreover, in certain embodiments, once inserted in vivo, the longitudinal arms of the sensor substrate sensor are free to flex and separate. In certain embodiments of the invention where the arms flex outward and in to an in vitro environment, the flexed arms function as anchoring elements that inhibit sensor movement in the environment. This allows the sensor to be positioned deeper in a tissue with a shorter implant. In addition, such pre-folding of the sensor may reduce the likelihood of sensor pullouts from the tissue environments in which they are disposed.

In typical sensor embodiments of the invention, a base substrate comprises a planar sheet of material having a first surface (e.g. the top side of a sheet of material) and a second surface (e.g. a bottom side of the sheet of material). In these embodiments of the invention, a plurality of electrically conductive sensor elements including electrodes, electrical conduits and connecting regions are formed on a single surface of the base structure, one which is typically made from a material such as a polyimide or other foldable polymeric substrate. In illustrative embodiments of the invention disclosed herein, elements are further processed, for example, by cutting the base substrate, by the addition of one or more layers of materials having selected functional properties (e.g. layers of a glucose oxidase composition) etc. By forming and/or processing sensor elements on a single side of a foldable sheet of material, sensor production is simplified and made more cost effective. In addition, with such embodiments, sensor elements are disposed in specific locations on the base structure so that the structure can be precisely folded at specific locations in order to create specific three dimensional constellations of sensor elements, constellations designed to facilitate sensing in certain contexts, for example, glucose sensing in in vivo tissues.

An illustrative embodiment of the invention is an analyte sensor apparatus comprising a base substrate formed from a planar sheet of a flexible material that is selected for its ability to transition from a first configuration to a second configuration when the base substrate is folded to form a fixed bend. In this embodiment of the invention, a working electrode, a counter electrode and a reference electrode are disposed upon a first surface of the base substrate. In such embodiments, the base substrate is folded to introduce a fixed bend that forms a specific 3-dimensional electrode configuration characterized in that at least one electrode is disposed on a first side of the fixed bend; and at least one electrode is disposed on a second side of the fixed bend (e.g. a sensor base substrate can be folded so as to create a fixed bend between counter and working electrodes).

As noted above, common embodiments of the invention comprise a specific 3-dimensional electrode configuration characterized in that at least one electrode is disposed on a first side of the fixed bend and at least one electrode is disposed on a second side of the fixed bend. Embodiments that do not include at least one electrode on each side of a fixed bend are also contemplated, for example in a foldover configuration having electrodes disposed only on a single side of a fixed bend. In one such embodiment of the invention, the base substrate can be folded, for example, to change the direction of the electrodes (e.g. so as to optimize the interaction with a sensing environment). In another embodiment of the invention having electrodes only on one side of a fixed bend, the base substrate can be folded so as to impart mechanical stability to the sensor when the sensor is implanted in vivo.

In typical embodiments of the invention, a plurality of contact pads are also disposed upon the first surface of the base substrate along with the electrodes, as well as a plurality of electrical conduits disposed upon the first surface of the base substrate. In such embodiments, the plurality of electrical conduits are adapted to transmit electrical signals between electrodes and contact pads that are separated by the fixed bend. Typically in such embodiments, an analyte sensing layer is disposed over the working electrode and includes one or more agents that detectably alter the electrical current at the working electrode in the presence of an analyte (e.g. glucose oxidase); and an analyte modulating layer is then disposed over the analyte sensing layer that modulates the diffusion of analyte therethrough.

The base substrate of the sensor apparatus can be made from a variety of materials and formed into a wide variety of shapes. In illustrative working embodiments of the invention such as the one shown in FIG. 1, the base substrate material can include a polymeric composition such as a polyimide and be formed (e.g. via laser cutting) into a shape that comprises a rectangular body, a first longitudinal arm extending outward from the rectangular body, and a second longitudinal arm extending outward from the rectangular body. In this illustrative working embodiment, the first longitudinal arm and the second longitudinal arm are of the same length and parallel to each other. In other illustrative embodiments, the first longitudinal arm and the second longitudinal arm are disposed at an angle relative to each other and/or are of different lengths.

Figure 8:
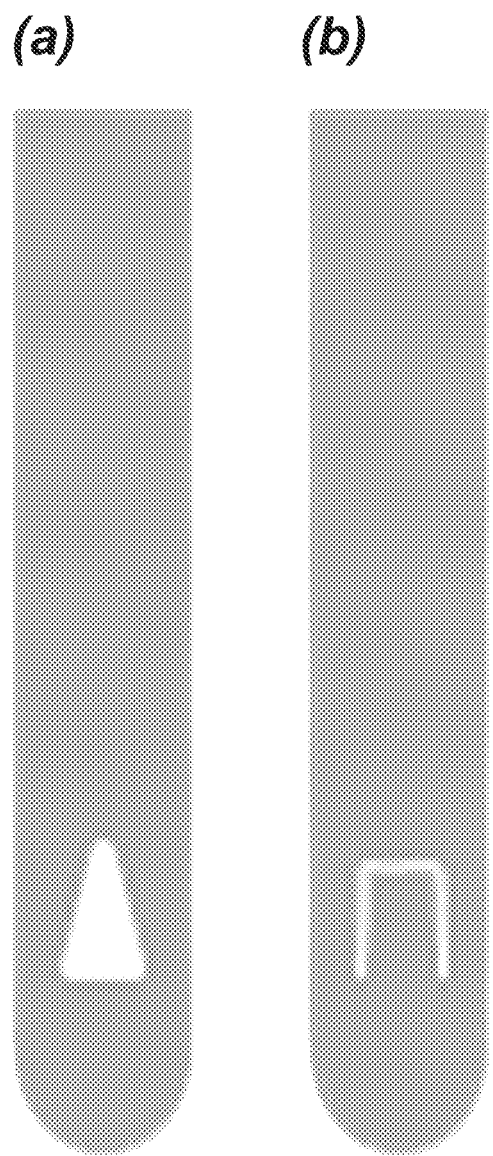
FIGS. 8A-8C illustrate embodiments of interlocking arms/members with FIG. 8(a) showing a hole in one longitudinal member.
Figure 8C:
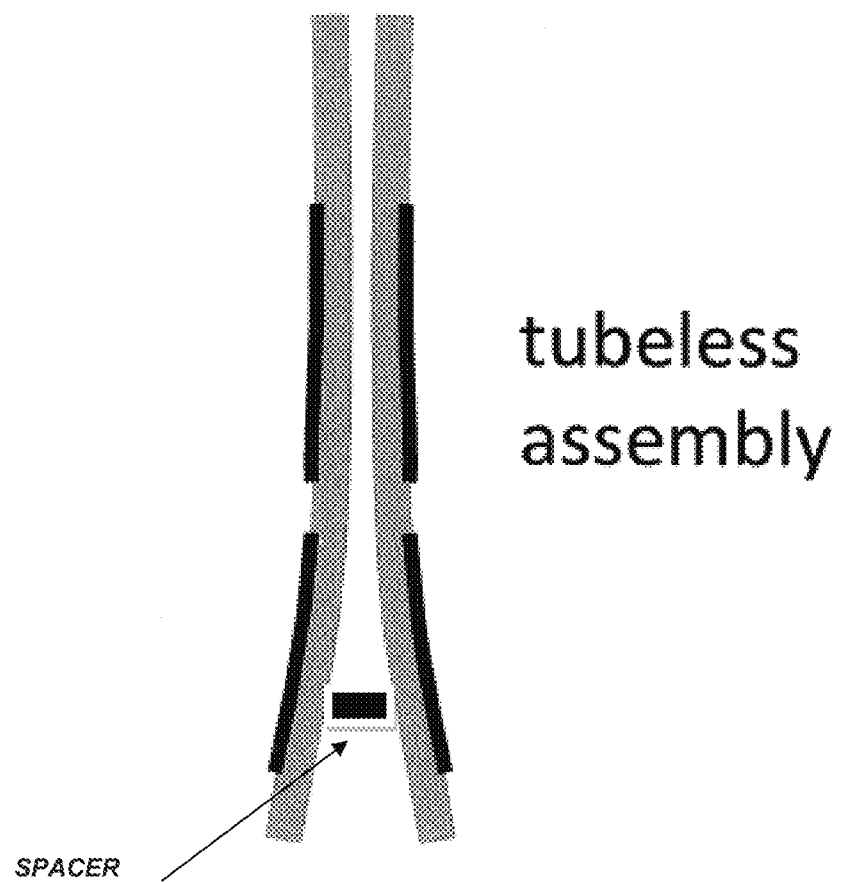

Optionally, the base substrate further comprises an identifying mark and/or a functional feature that facilitates folding, for example a demarcation, a perforation, or a kiss cut that helps a user identify and/or manipulate the region at which the base substrate is folded. In some embodiments of the invention, the sensor apparatus comprises a locking member that is adapted to inhibit movement of one or more elements that form or are coupled to the folded base (e.g. to inhibit movement of the first longitudinal arm or the second longitudinal arm). One illustrative embodiment of such a locking member is shown in FIGS. 8A & 8B. In certain embodiments of the invention, the sensor apparatus comprises a spacing member that is adapted to maintain a distance between the electrodes on the first longitudinal arm and the second longitudinal arm, so that the distance between the arms (or the electrodes disposed on the arms) is at least 0.1, 0.2, 0.3, 0.4, 0.5, 0.6, 0.7, 0.8, 0.9, 1, 1.25, 1.5, 1.75, 2, 2.5, 3, 3.5, 4, 4.5, 5, 6, 7, 8, 9 or 10 millimeters. Optionally, the spacing member comprises a column of material (e.g. a rigid tubing of a defined length) that is disposed on and/or spaced between the first longitudinal arm and the second longitudinal arm (see, e.g. FIG. 8C).

Figure 3:
Figure 3C:
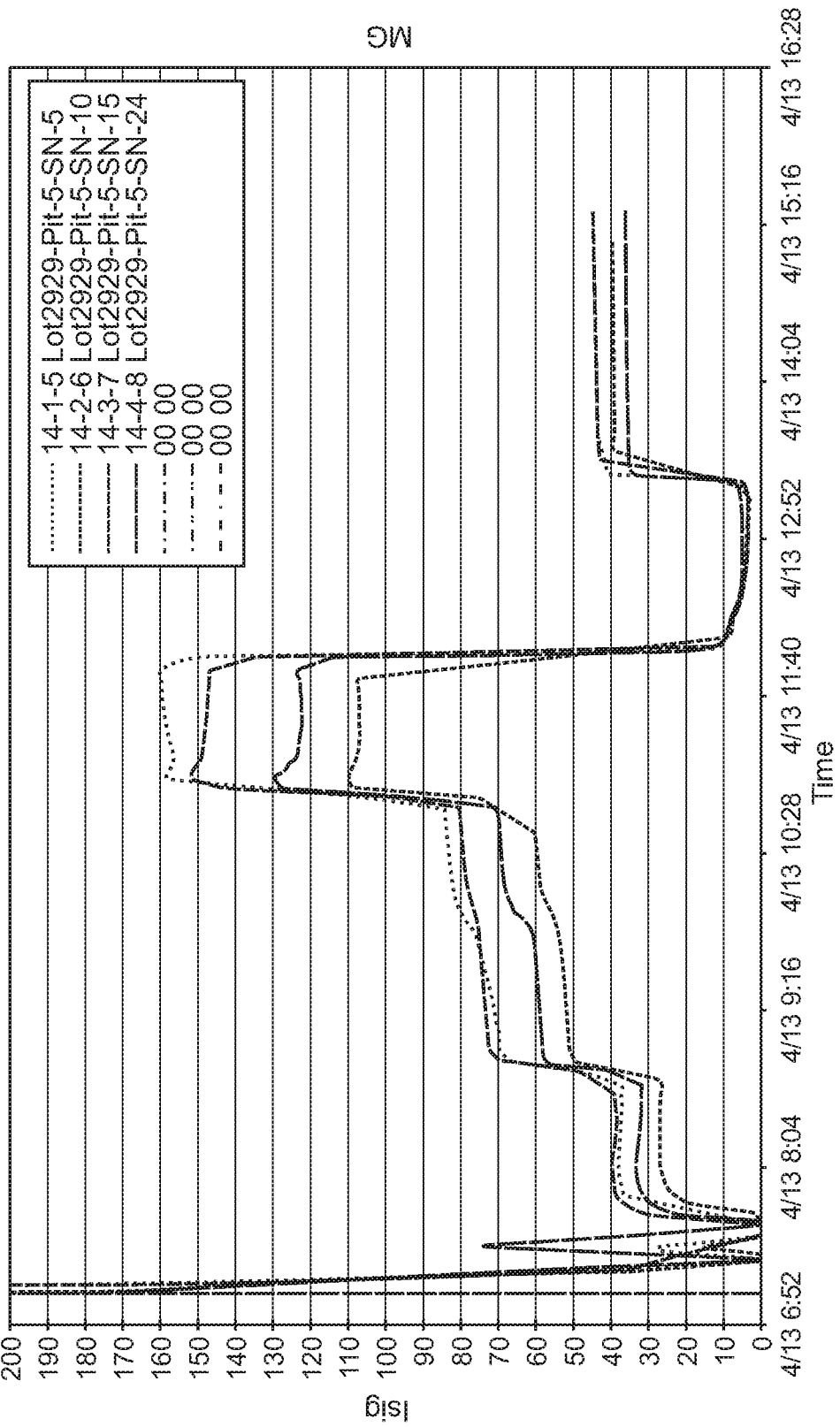
Figure 3D:
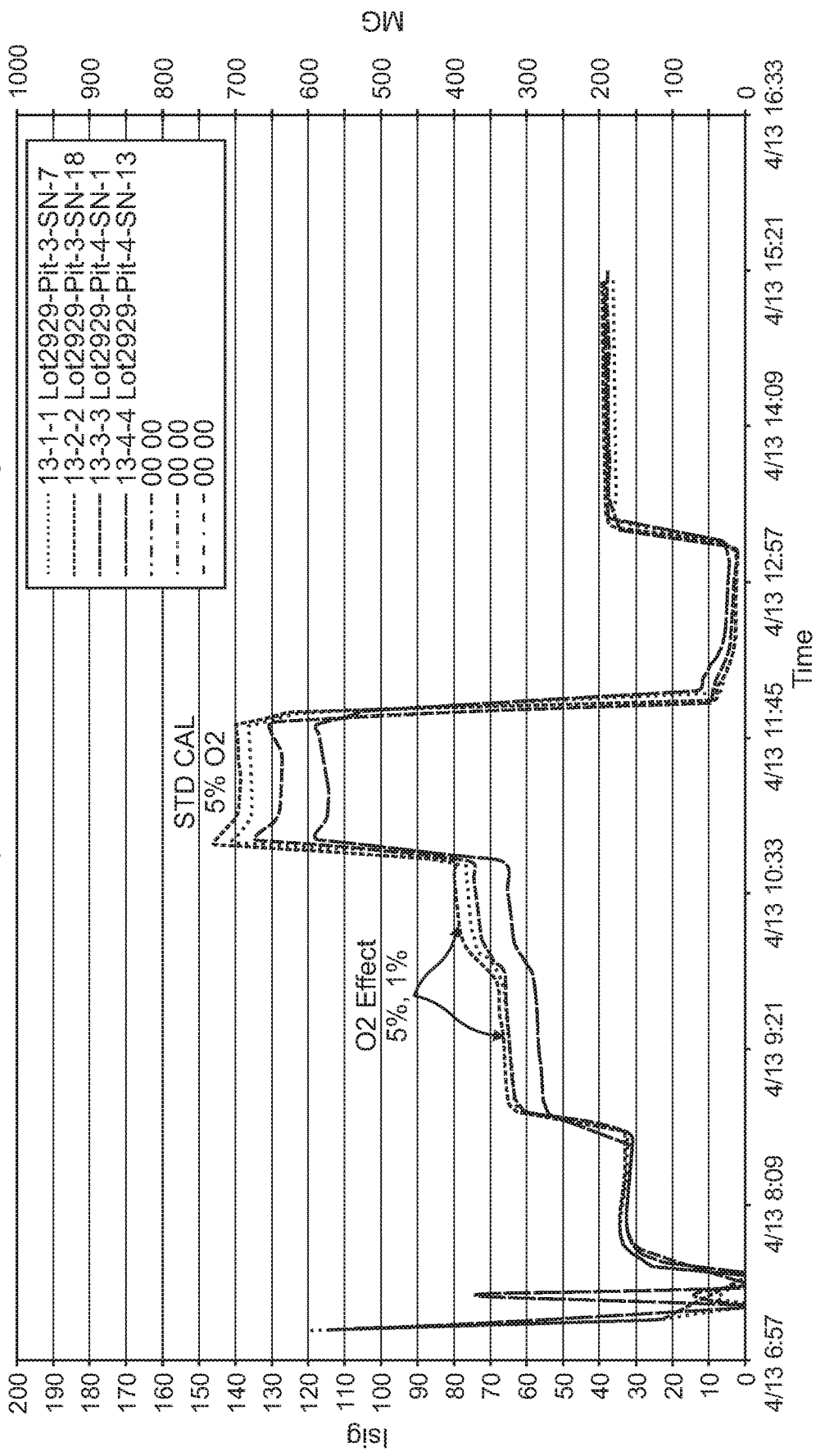

In typical embodiments of the invention, the apparatus comprises a plurality of working electrodes, for example, a first working electrode disposed on the first longitudinal arm and a second working electrode disposed on the second longitudinal arm (and/or multiple working electrodes is disposed on one longitudinal arm). In some embodiments of the invention, the base substrate comprises a plurality of reference electrodes, a plurality of working electrodes and a plurality of counter electrodes clustered together in units consisting essentially of one working electrode, one counter electrode and one reference electrode. Optionally the clustered units are longitudinally distributed on the base substrate in a repeating pattern of units. In such embodiments, one working electrode can be coated with a first set of layered materials and another working electrode can be coated with a second set of layered materials (e.g. different sets of materials that are designed to sense glucose in different concentration ranges). In certain embodiments of the invention, the fixed bend in the base substrate configures the substrate in an orientation so that at least one electrode on the first side of the fixed bend and at least one electrode on the second side of the fixed bend face opposite directions (see, e.g. FIG. 3). Such embodiments can be used for example to provide a greater distance between electrodes (e.g. counter and working electrodes), a configuration which may inhibit electron migration that can negatively impact sensor signals.

Embodiments of the invention can include other structural elements designed for use in specific analyte environments. In some embodiments, at least a portion of the base substrate (e.g. the longitudinal arms of a base substrate or the sensor electrodes that are located on such arms) are disposed within a housing (e.g. a tube) and adapted to be implanted in vivo (e.g. the "tubed" embodiment shown in FIG. 6A). Typically, in such embodiments, the housing comprises an aperture adapted to allow an aqueous medium in which the apparatus is disposed to contact a working electrode. In such embodiments, sensors can be placed in tubes with apertures/windows on one or both sides to increase circulation and allow fluid access to both sides of the sensor. In alternative embodiments of the invention the apparatus does not comprise a housing that surrounds a portion of the base substrate (e.g. the "tubeless" embodiment shown in FIG. 6B). In such embodiments, sensor elements (e.g. longitudinal arms of a base substrate) can be held together through capillary action during assembly, while after implantation they are free to separate. In these embodiments, the sensor is disposed within a needle adapted to pierce a tissue and implant the apparatus in vivo. Optionally in such embodiments, the needle is adapted to be removed from the tissue following implantation of the analyte sensor apparatus.

Embodiments of the invention include further elements designed for use with the folded sensors that are disclosed herein, for example those that are designed to analyze electrical signal data obtained from electrodes disposed on the folded base substrate. In some embodiments of the invention, the analyte sensor apparatus includes a processor and a computer-readable program code having instructions, which when executed, cause the processor to assess electrochemical signal data obtained from at least one working electrode and then compute analyte concentrations based upon the electrochemical signal data obtained from the working electrode. In certain embodiments of the invention, the processor compares electrochemical signal data obtained from multiple working electrodes in order to, for example, adapt different electrodes to sense different analytes, and/or to focus on different concentration ranges of a single analyte, and/or to identify or characterize spurious sensor signals (e.g. sensor noise, signals caused by interfering compounds and the like) so as to enhance the accuracy or reliability of the sensor readings.

Related embodiments of the invention include methods of making a folded analyte sensor apparatus as disclosed herein. Briefly, in typical methods: (1) sensor electrodes and traces are patterned on to a substrate formed from a polyimide or other flexible material; (2) chemistry layers are then applied to the electrodes (e.g. layers comprising glucose oxidase, layers comprising a glucose limiting membrane); and (3) the sensors are then laser cut and folded prior to final assembly, a step which results in electrodes disposed on the front and back of the base substrate. Methods for making the sensors disclosed herein include the initial steps of providing a base substrate formed from a planar sheet of a flexible material having a first surface and a second surface and adapted to transition from a first configuration to a second configuration when the base substrate is folded. In the working embodiments of the invention that are disclosed herein, the base substrate is designed to include a rectangular body, a first longitudinal arm extending outward from the rectangular body, and a second longitudinal arm extending outward from the rectangular body. In illustrative embodiments of the invention, the shape of the base substrate is formed by cutting the shape out of a sheet of material, for example by laser cutting. In some embodiments of the invention, the electrodes, contact pads, traces and the like are formed on the substrate before it is shaped into its final form. In other embodiments of the invention, the electrodes, contact pads, traces and the like are formed on the substrate after it is shaped into its final form. FIG. 1 provides an illustrative embodiment of a sensor substrate of the invention. As shown in this figure, the base matrix has a shape that includes a rectangular body (500), a first longitudinal arm extending outward from the rectangular body (520); and a second longitudinal arm (530) extending outward from the rectangular body. In this embodiment, the rectangular body and the longitudinal arms are linked by a neck region (510).

Typical embodiments of the invention include forming a plurality of contact pads and/or a plurality of electrical conduits upon the first surface of the base substrate. In such embodiments of the invention, the plurality of electrical conduits are selected to be of a size and formed from material that allows them to transmit electrical signals between electrodes and contact pads separated by the architecture of the fixed bend (e.g. an amount of an electrically conductive material that will flex, not break when bent). In particular, in some embodiments of the invention that were observed to exhibit unusual signal variation, deformations in the electrical conduits were observed in the regions where the conduits were folded. It is possible that these deformations are associated with the observed electronic signal variation. The shape, size and material of these conduits is therefore tailored to the specific architectures in which they are used (e.g. by increasing the width/girth/material of electrical conduits that are disposed over complex 3-dimensional architectures).

The methods of the invention include the steps of forming a working electrode, a counter electrode and a reference electrode on the first surface of the base substrate. Typically, at least one of these electrodes is formed on a first longitudinal arm and at least one other electrode is formed on a second longitudinal arm. These methods further include adding layers of materials onto one or more electrodes, for example, forming an analyte sensing layer on the working electrode that detectably alters the electrical current at the working electrode in the presence of an analyte as well as forming an analyte modulating layer on the analyte sensing layer that modulates the diffusion of analyte therethrough. In certain embodiments of the invention, the analyte sensing layer comprises glucose oxidase. In some embodiments of the invention, the apparatus comprises an adhesion promoting layer disposed between the analyte sensing layer and the analyte modulating layer. Optionally, the analyte modulating layer comprises a hydrophilic comb-copolymer having a central chain and a plurality of side chains coupled to the central chain, wherein at least one side chain comprises a silicone moiety.

Methods for making sensor embodiments of the invention can include folding the base substrate so as to introduce a fixed bend that results in a configuration where at least one electrode is disposed on a first side of the fixed bend, and at least one electrode is disposed on a second side of the fixed bend. These methods can be used to produce a wide variety of the folded sensor structures. For example, in some embodiments of the invention, the base substrate is formed so that the first longitudinal arm and the second longitudinal arm are parallel to each other. Optionally, the base substrate is folded so that the first longitudinal arm and the second longitudinal arm are superimposed on each other. In certain embodiments of the invention, the base substrate is folded to introduce a fixed bend that configures the substrate in an orientation so that at least one electrode on the first side of the fixed bend and at least one electrode on the second side of the fixed bend face opposite directions. In other embodiments of the invention, the base substrate is folded so that the first side of the base substrate that results from the fixed bend is in a plane at least 40, 50, 60, 70, 80 or 90 degrees off of the second side of the substrate that results from the fixed bend.

Embodiments of the invention are adapted for use with certain electrode configurations. For example, in some embodiments of the invention, the working electrode is formed as an array of electrically conductive members disposed on the base substrate, the electrically conductive members are circular and have a diameter between 10 μm and 400 μm; and the array comprises at least 5, 10 or 15 electrically conductive members. In certain embodiments of the invention, a plurality of working electrodes, counter electrodes and reference electrodes clustered together in units consisting essentially of one working electrode, one counter electrode and one reference electrode are formed on the base substrate, and the clustered units are longitudinally distributed on at least one longitudinal arm of the base substrate in a repeating pattern of units. In some embodiments of the invention, a first clustered unit is disposed on a first longitudinal arm and a second clustered unit is disposed on a second longitudinal arm.

Figure 2:
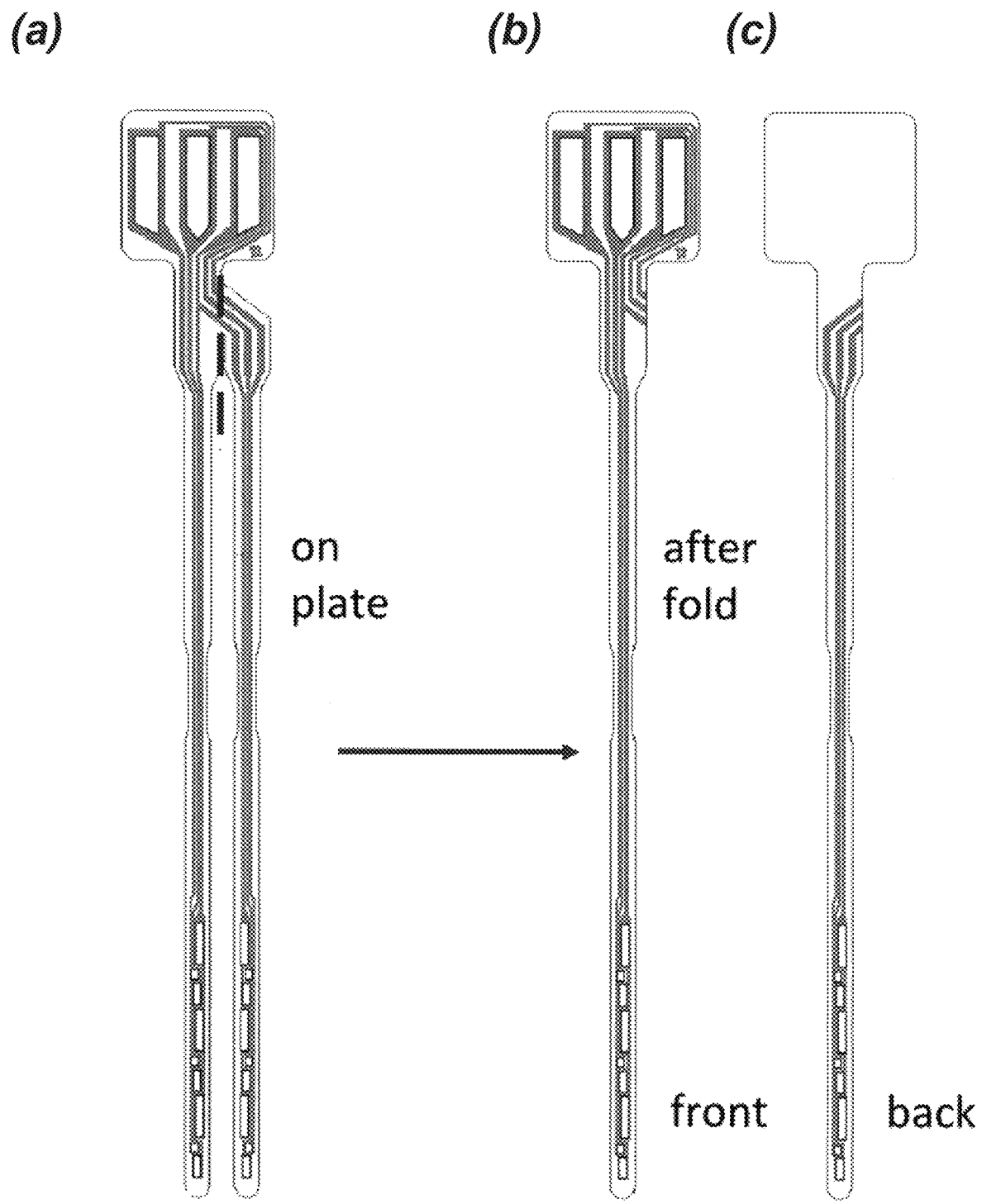
Figure 7:
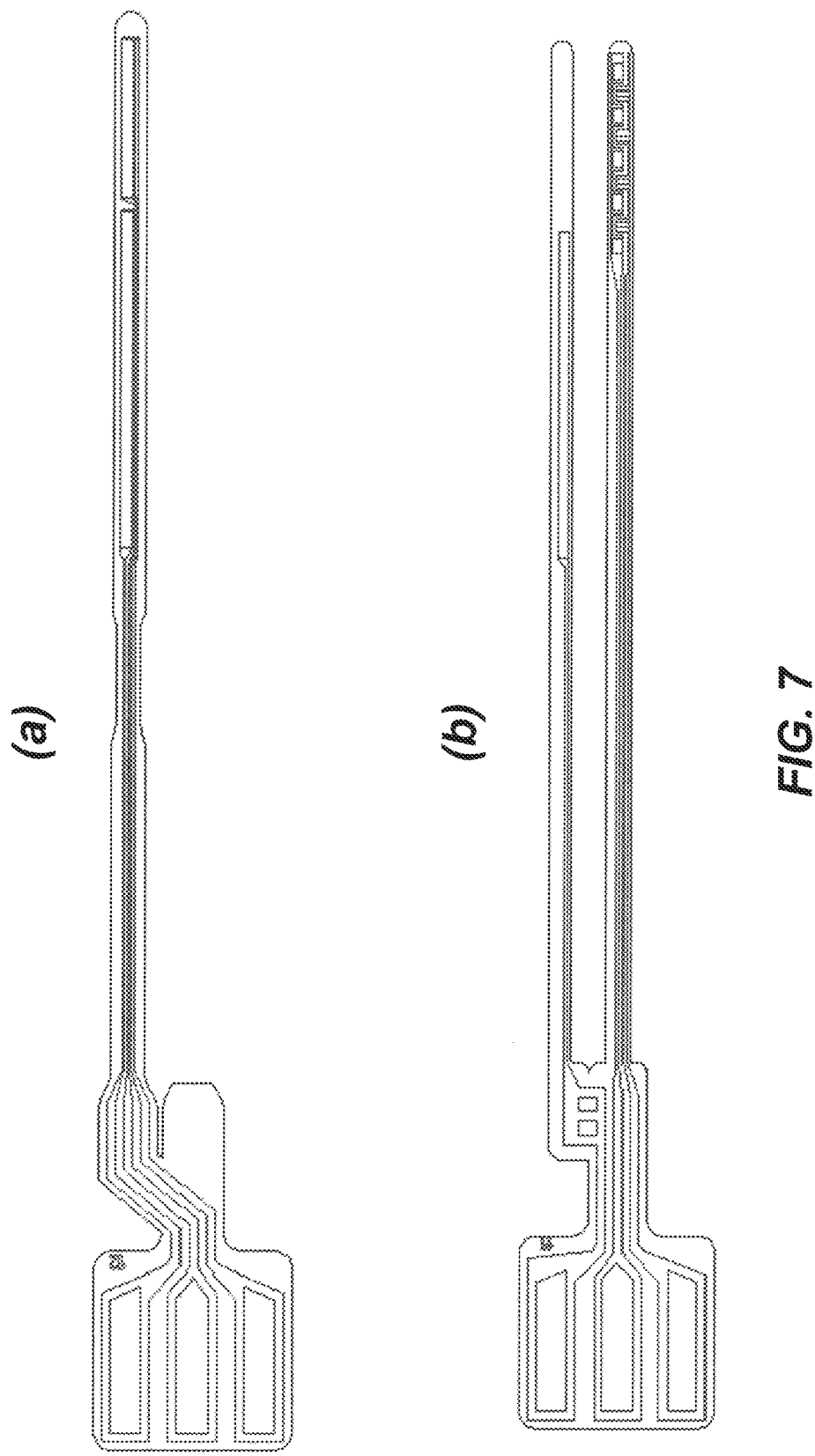
FIGS. 7A-7B illustrate various embodiments of a sensor, with FIG. 7(a) showing a foldover sensor with electrodes only on the back surface and FIG. 7(b) showing a foldover sensor with a counter electrode on the back surface and working electrodes on the front surface.

As noted above, in embodiments of the invention, a base structure can be of a variety of shapes, depending upon the final constellation of elements that is desired. Optionally, for example the base structure can comprise a first longitudinal member and a second longitudinal member as shown for example in FIGS. 1-3. In embodiments such as those shown in FIGS. 1-3, the first and second longitudinal members each comprise at least one electrode, and typically include a plurality of working, counter and reference electrodes (e.g. at least 2, 3, 4 or 5 groups) that are grouped together as a unit (e.g. at least 2, 3, 4 or 5 groups of working, counter and reference electrodes) and positionally distributed on a repeating pattern of units on the front surface (see, e.g. US. Patent Application Publication No. 2010/0025238, the contents of which are incorporated herein by reference). As shown in FIG. 2, in some embodiments of the invention the electrodes are of different sizes, for example, a counter electrode that is at least 2× the size of a working or reference electrode and/or a working electrode that is at least 2× (or ½×) the size of a reference electrode. In another embodiment of the invention, the counter electrode is 2× the size of the working electrode and the reference electrode is ⅓ the size of the working electrode. In the embodiment shown in FIGS. 2A-2C the base structure is folded along a longitudinal axis (dotted line in FIG. 2A) such that the first longitudinal member is substantially superimposed over the second longitudinal member. Typically, the base structure comprises a dielectric composition. In common embodiments of the invention, the folded sensor base substrates do not include vias, electrical connections in which must extend through dielectric layers to connect conductive layers on either side of a dielectric material, thereby facilitating sensor production. In some embodiments of the invention, first and second longitudinal members comprise substantially similar electrical elements (see, e.g. FIG. 1 which shows both members comprising a plurality of working, counter and reference electrodes positionally distributed on a repeating pattern of units). In other embodiments of the invention, first and second longitudinal members comprise substantially different electrical elements (see, e.g. FIG. 7 which shows working electrode(s) on a first member and counter electrodes on a second member).

Figure 4:
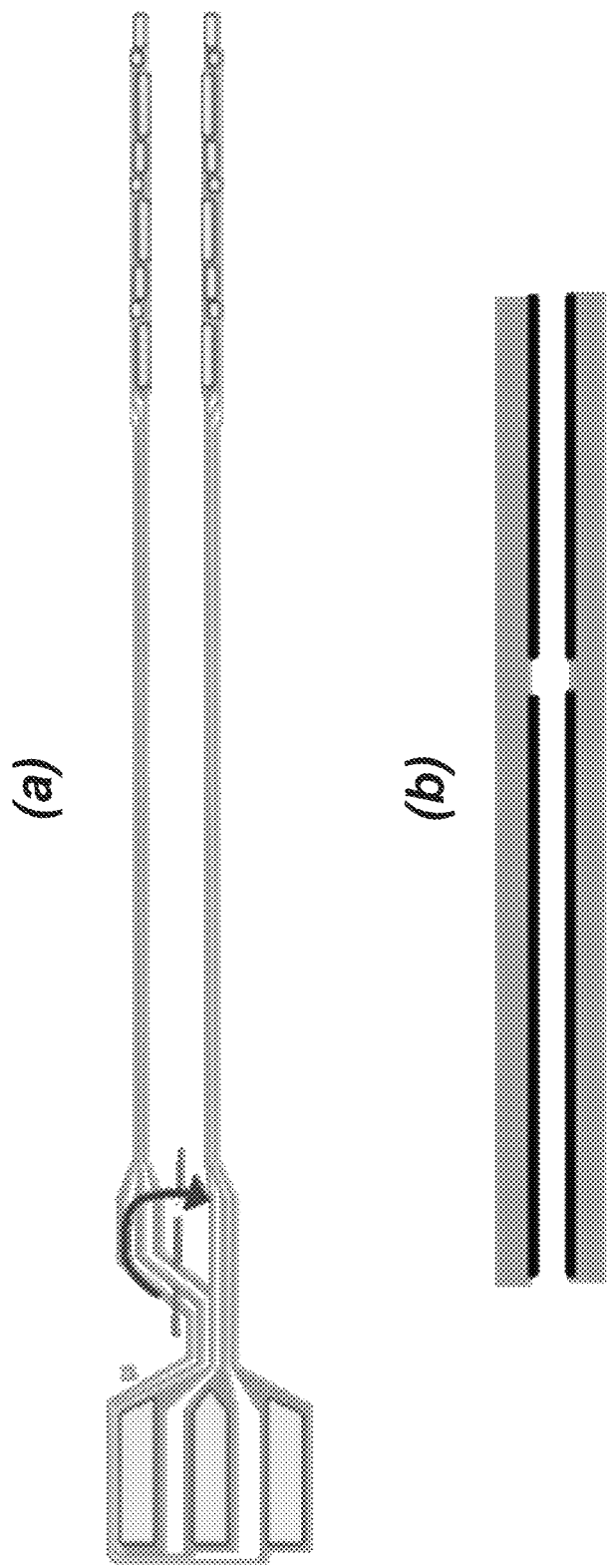
FIGS. 4A-4B illustrate another embodiment of a sensor, with FIG. 4(a) showing a top-down view of a foldover sensor prior to folding over a longitudinal axis represented by a dotted line and FIG. 4(b) showing a side view of the foldover sensor with the electrodes (black) facing in after folding.

As shown in FIGS. 2B-2C, in certain embodiments of the invention, the base structure can be folded along a longitudinal axis such that electrodes on the first longitudinal arm/member are disposed in a substantially opposite orientation or direction from electrodes on the second longitudinal member, for example so that the electroactive surfaces of the electrodes are substantially oriented 180 degrees from each other (e.g. face away from each other as shown in FIG. 3B). Alternatively, the base structure can be folded along a longitudinal axis such that the at least one electrode on the front surface of the first longitudinal member is disposed in the direction of at least one electrode on the front surface of the second longitudinal member (e.g. so that the electroactive surfaces of the electrodes substantially face each other as shown in FIG. 4B). Alternatively, the base structure can be folded along a longitudinal axis such that the at least one electrode on the front surface of the first longitudinal member is disposed in a relatively perpendicular orientation to at least one electrode on the front surface of the second longitudinal member.

Figure 5:
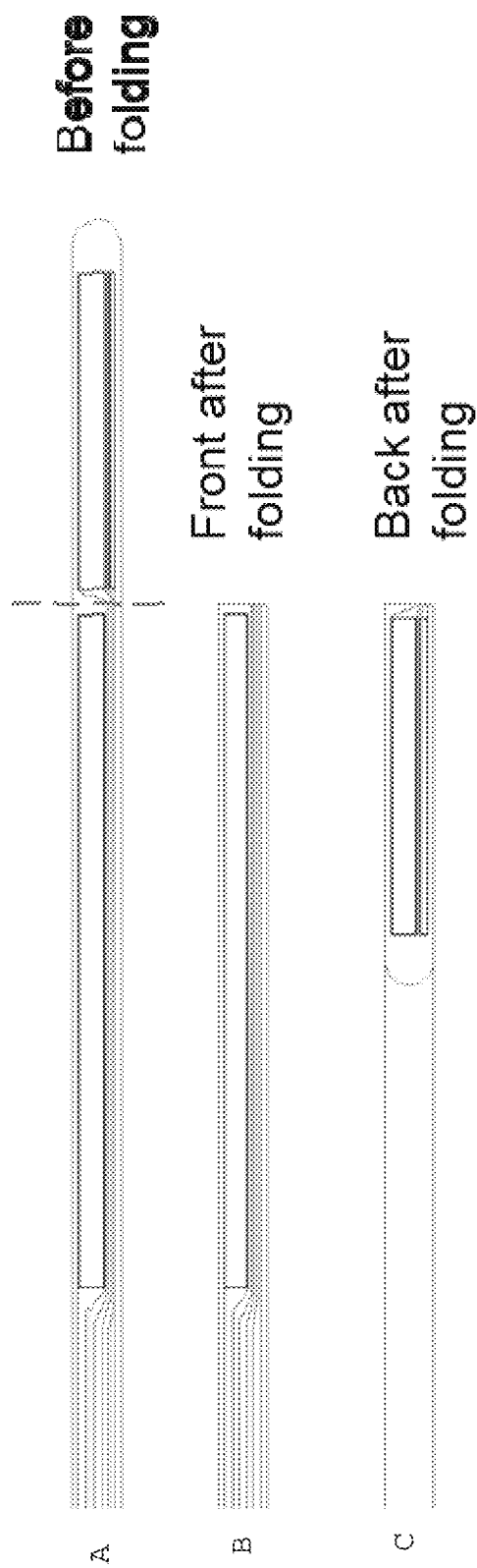
FIGS. 5A-5C illustrate another embodiment of a sensor, with FIG. 5(a), showing a top-down view of a longitudinal member of a foldover sensor prior to folding over an axis of a longitudinal arm represented by a dotted line perpendicular to its longitudinal direction; as well as FIG. 5(b), showing a top-down view of the front surface of the foldover sensor after folding, and FIG. 5(c), showing a back surface foldover sensor after folding.

Embodiments of the invention can include a variety of different configurations comprising bases of different shapes and sizes having one or a plurality of folds (e.g. 2, 3, 4, 5, or more folds). As shown in FIG. 5, in certain embodiments of the invention, one or more longitudinal members can be folded back on themselves, for example so that electrodes are disposed on opposite sides of a single longitudinal member. An illustrative embodiment of the invention comprises a foldover sensor including a base structure having a front surface and a back surface, the base structure comprising at least one longitudinal member (and typically two or more), wherein the front surface of the longitudinal member comprises at least one electrode (but typically comprises a plurality of working and/or reference, and/or counter electrodes) and further is folded perpendicular to its longitudinal direction or in a manner that orients a portion of the first longitudinal member over another portion of the first longitudinal member (e.g. so that electrodes are disposed on opposite sides of a longitudinal member, see, e.g. FIG. 5).

Figure 6:
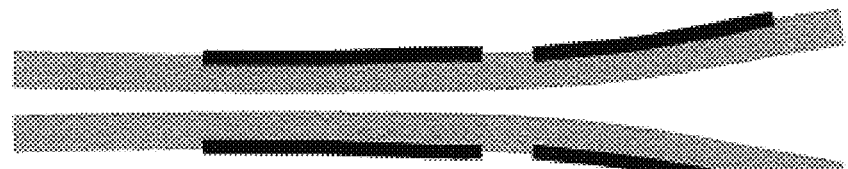
FIGS. 6A-6B illustrate embodiments of sensor elements, with FIG. 6(a) showing a tubed assembly comprising longitudinal members placed in tubes with windows on both sides to increase circulation and allow fluid access to both sides of the longitudinal members and FIG. 6(b) showing, a tubeless assembly comprising longitudinal members held together through capillary action during assembly and free to separate after implementation.
Figure 6:
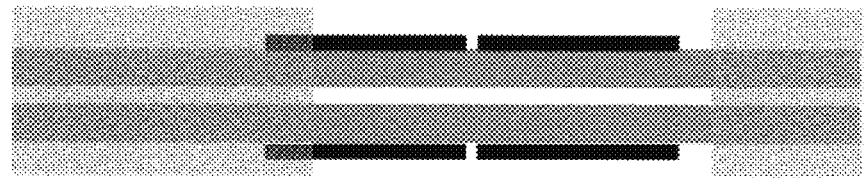

In some embodiments of the invention, the composition of the base structure is selected to have material properties that influence sensor configuration. Optionally in these embodiments, the base is formed from, or coated with, a dielectric material. For example, in certain embodiments of the invention, the base is made from a dielectric polymeric material that is designed to flex in a certain direction following the sensor fold and/or when the sensor is disposed in the environments in which an analyte is sensed. In one illustrative example shown in FIG. 6B, the material of the base structure can flex so as to increase the distance between first and second longitudinal members on which the electrodes are disposed (e.g. so that the distance between a pair of electrodes and/or the first and second longitudinal members is at 0.1, 0.2, 0.3, 0.4, 0.5, 0.6, 0.7, 0.8, 0.9, 1, 23, 4, 5, 6, 7 or 10 millimeters). In addition, some embodiments of the invention include positioning or locking members that facilitate proper sensor architecture. Optionally, for example, a first longitudinal member of a base structure comprises a first interlocking member and a second longitudinal member comprises a second interlocking member that positions the members in a specific orientation. In illustrative embodiments, coupling the first interlocking member to the second interlocking member keeps the first longitudinal member substantially superimposed over the second longitudinal member. FIG. 6 shows a sensor assembly where a tube is used to control sensor architecture. FIGS. 8A&B show an embodiment of an illustrative mechanism designed to position or lock portions of the sensor together (in this case the base material) so as to help maintain a desired sensor architecture.

As noted above, in embodiments of the invention, electrically conductive sensor elements such as electrodes and/or electrical conduits (e.g. traces) and/or connecting regions (e.g. contact pads) are formed on a single surface of the base structure. In such embodiments, electrically conducting sensor elements are disposed in specific locations on the base structure so that the base can be subsequently folded at specific locations in order to create a three dimensional constellation of sensor elements. In typical embodiments of the invention, the base structure is generally implemented as an electrically insulating (i.e., non-conducting) material such as polyimide, rubber, TEFLON, MYLAR, and the like. The base structure may be implemented using a wide variety appropriate (or suitable) flexible dielectric materials known in the art depending upon, for example, the architecture of a particular folded sensor design. In embodiments of the invention, the materials used to make the electrically conductive sensor elements and/or the structures of these elements can be selected due to an ability to be amenable to folding. For example, in addition to selecting optimized locations for the folded elements, the length, thickness and/or width of these elements (e.g. traces in a conductive path) as well as the number and spacing of the elements can be adapted for optimized functioning in various three dimensional sensor architectures such as those disclosed herein. Typically, the electrical elements such as trace conductors can be made from (i.e., produced from, implemented using, etc.) at least one flexible electrically conductive material (e.g., Cu, Si, Cu, Al, Cr, Ti, Pt, Ir and the like). For example, trace conductors may be implemented using any appropriate (or suitable) electrically conductive material known in the art depending upon, for example, the architecture of a particular folded sensor design.

Embodiments of the invention include methods for making the foldover sensors disclosed herein. Such sensors can be made by adapting certain methods known in the art, for example, those disclosed in U.S. Pat. No. 6,484,045, the contents of which are incorporated by reference. One illustrative embodiment is method of making a foldover sensor, the method comprising the steps of providing a base structure having a front surface and a back surface and then patterning a plurality of electrically conductive elements including at least one electrode (and optionally a plurality of working counter and reference electrodes and/or a plurality of electrical conduits (e.g. traces and the like) and/or a plurality of contact pads and the like) on the front surface of the base structure. In such methods one can form the base structure into a particular shape/geometry, for example by forming the base material in a mold and/or by cutting the base structure, for example to form a first longitudinal member and a second longitudinal member, each comprising electrically conductive elements. In such methods one can pattern the conductive elements onto specific regions of the base structure that will result in a specific three dimensional architecture when folded.

These methods can comprise folding the base structure to generate a constellation of electrical elements having a specific three dimensional architecture, for example by folding a base with longitudinal members along a longitudinal axis such that the first longitudinal member is substantially superimposed over the second longitudinal member. In one illustrative embodiment, the base structure is folded along a longitudinal axis such that the front surface of a first longitudinal member faces in a substantially opposite direction away from the front surface of a second longitudinal member. Alternatively, the base structure is folded along a longitudinal axis such that the front surface of the first longitudinal member faces towards the front surface of the second longitudinal member. Embodiments of the invention include forming the sensor to include additional elements, for example an embodiment where a first longitudinal member comprises a first interlocking member and the second longitudinal member comprises second interlocking member complementary to the first interlocking member, and further comprising coupling the first interlocking member to the second interlocking member such that the first longitudinal member maintains a position substantially superimposed over the second longitudinal member. Other embodiments of the invention include disposing the folded base structure in a hollow tube (e.g. a needle, a catheter or the like).

Embodiments of the invention include methods of adding a plurality of materials to the surface(s) of the electrode(s) disposed on the base, either prior to, or subsequent to folding (and sensors made from such methods). One such embodiment of the invention is a method of making a sensor apparatus (e.g. a glucose sensor) for implantation within a mammal comprising the steps of: providing a base substrate; forming a conductive layer on the base substrate, wherein the conductive layer includes an electrode (and typically a working electrode, a reference electrode and a counter electrode); forming an analyte sensing layer on the conductive layer, wherein the analyte sensing layer includes a composition that can alter the electrical current at the electrode in the conductive layer in the presence of an analyte (e.g. glucose oxidase); optionally forming a protein layer over the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In different embodiments of the invention, the base material can be folded following the application of a specific material, for example an analyte modulating layer, a cover layer, etc. See, e.g. U.S. Patent Publication No. 2010/0025238, the contents of which are incorporated by reference.

In some embodiments of the invention, the base structure comprises a foldable yet rigid and flat structure suitable for use in photolithographic mask and etch processes. In this regard, the base structure typically includes at least one surface having a high degree of uniform flatness. Base structure materials can include, for example, metals such as stainless steel, aluminum and nickel titanium memory alloys (e.g. NITINOL) as well as polymeric/plastic materials such as delrin, etc. Base structure materials can be made from, or coated with, a dielectric material. In some embodiments, the base structure is non-rigid and can be a layer of film or insulation that is used as a substrate for patterning electrical elements (e.g. electrodes, traces and the like), for example plastics such as polyimides and the like. An initial step in the methods of the invention typically includes the formation of a base substrate of the sensor. Optionally the planar sheet of material is formed and/or disposed on a support such as a glass or ceramic plate during sensor production (see, e.g. FIG. 2A). The base structure can be disposed on a support (e.g. a glass plate) by any desired means, for example by controlled spin coating. Optionally, a base substrate layer of insulative material is formed on the support, typically by applying the base substrate material onto the support in liquid form and thereafter spinning the support to yield a base substrate structure that is thin and of a substantially uniform thickness. These steps can be repeated to build up a base substrate structure to a desired thickness. This can then be followed by a sequence of photolithographic and/or chemical mask and etch steps to form the electrically conductive components. In an illustrative form, the base substrate comprises a thin film sheet of insulative material, such as a polyimide substrate that is used to pattern electrical elements. The base substrate structure may comprise one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof.

The methods of the invention further include the generation of an electrically conductive layer on the base substrate that function as one or more sensing elements. Typically these sensing elements include electrodes, electrical conduits (e.g. traces and the like), contact pads and the like that are formed by one of the variety of methods known in the art such as photolithography, etching and rinsing to define the geometry of the active electrodes. The electrodes can then be made electrochemically active, for example by electrodeposition of Pt black for the working and counter electrode, and silver followed by silver chloride on the reference electrode.

A sensor layer such as a analyte sensing enzyme layer can then be disposed on the sensing layer by electrochemical deposition or a method other than electrochemical deposition such a spin coating, followed by vapor crosslinking, for example with a dialdehyde (glutaraldehyde) or a carbodiimide.

In an exemplary embodiment of the invention, the base substrate is initially coated with a thin film conductive layer by electrode deposition, surface sputtering, or other suitable patterning or other process step. In one embodiment this conductive layer may be provided as a plurality of thin film conductive layers, such as an initial chrome-based layer suitable for chemical adhesion to a polyimide base substrate followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base substrate. In an illustrative sensor construction designed for use as a subcutaneous glucose sensor, each sensor trace can include two or three parallel sensor elements corresponding with two or three separate electrodes such as a working electrode, a counter electrode and a reference electrode.

Additional functional coatings or cover layers can then be applied to an electrode or other senor element by any one of a wide variety of methods known in the art, such as spraying, dipping, etc. Some embodiments of the present invention include an analyte modulating layer deposited over a enzyme-containing layer that is disposed over a working electrode. In addition to its use in modulating the amount of analyte(s) that contacts the active sensor surface, by utilizing an analyte limiting membrane layer, the problem of sensor fouling by extraneous materials is also obviated. As is known in the art, the thickness of the analyte modulating membrane layer can influence the amount of analyte that reaches the active enzyme. Consequently, its application is typically carried out under defined processing conditions, and its dimensional thickness is closely controlled. Microfabrication of the underlying layers can be a factor which affects dimensional control over the analyte modulating membrane layer as well as exact the composition of the analyte limiting membrane layer material itself. In this regard, it has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures described herein.

In some embodiments of the invention, the sensor is made by methods which apply an analyte modulating layer that comprises a hydrophilic membrane coating which can regulate the amount of analyte that can contact the enzyme of the sensor layer. For example, a cover layer that is added to the glucose sensing elements of the invention can comprise a glucose limiting membrane, which regulates the amount of glucose that contacts glucose oxidase enzyme layer on an electrode. Such glucose limiting membranes can be made from a wide variety of materials known to be suitable for such purposes, e.g., silicones such as polydimethyl siloxane and the like, polyurethanes, cellulose acetates, Nafion, polyester sulfonic acids (e.g. Kodak AQ), hydrogels or any other membrane known to those skilled in the art that is suitable for such purposes. In certain embodiments of the invention, the analyte modulating layer comprises a hydrophilic polymer. In some embodiments of the invention the analyte modulating layer comprises a linear polyurethane/polyurea polymer and/or a branched acrylate polymer, and/or a mixture of such polymers.

In some embodiments of the methods of invention, an adhesion promoter layer is disposed between a cover layer (e.g. an analyte modulating membrane layer) and a analyte sensing layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art.

The finished sensors produced by such processes are typically quickly and easily removed from a support structure (if one is used), for example, by cutting along a line surrounding each sensor on the support structure. The cutting step can use methods typically used in this art such as those that include a laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. Since the base substrate is typically not physically attached or only minimally adhered directly to the underlying support, the sensors can be lifted quickly and easily from the support structure, without significant further processing steps or potential damage due to stresses incurred by physically pulling or peeling attached sensors from the support structure. The support structure can thereafter be cleaned and reused, or otherwise discarded. The functional coating layer(s) can be applied either before or after other sensor components are removed from the support structure (e.g. by cutting).

Embodiments of the invention include methods of sensing an analyte (e.g. glucose) within the body of a mammal (e.g. a diabetic patient), the method comprising implanting a foldover analyte sensor embodiment disclosed herein into an in vivo environment and then sensing one or more electrical fluctuations such as alteration in current at the working electrode and correlating the alteration in current with the presence of the analyte, so that the analyte is sensed. Typically, this method comprises implanting a glucose sensor having a folded architecture within the interstitial space of a diabetic individual, sensing an alteration in current at the working electrode in the presence of glucose; and then correlating the alteration in current with the presence of the glucose, so that glucose is sensed. While typical embodiments of the invention pertain to glucose sensors, the folded sensor designs disclosed herein can be adapted for use with a wide variety of devices known in the art.

Figure 9:
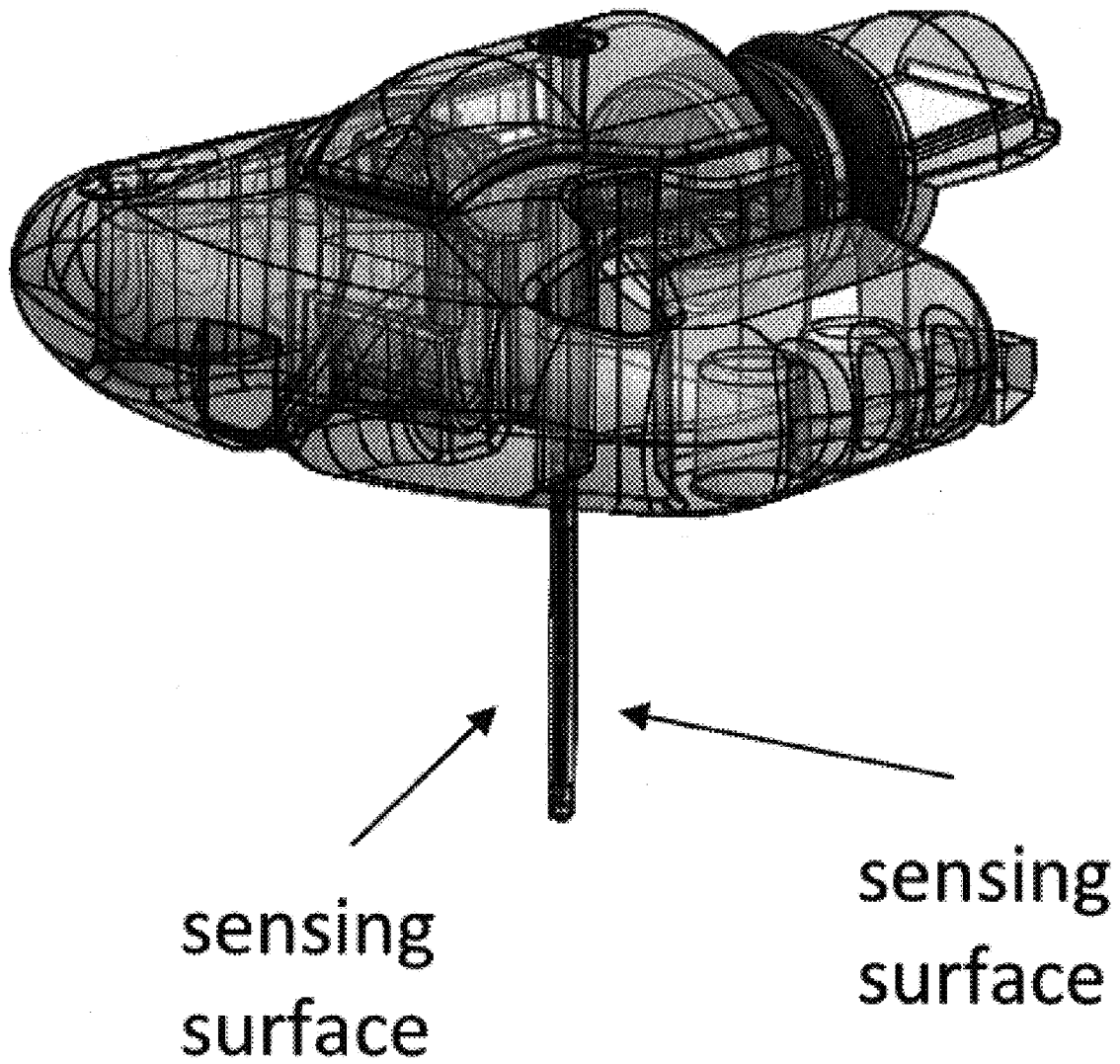
FIG. 9 illustrates one embodiment of a foldover sensor having multiple sensing surfaces incorporated in a glucose sensor system.

As discussed in detail below, embodiments of the invention include sensor systems comprising addition elements designed to facilitate sensing of an analyte. For example, in certain embodiments of the invention, the base material comprising the sensor electrodes is disposed within a housing (e.g. a lumen of a catheter) and/or associated with other components that facilitate analyte (e.g. glucose) sensing. FIG. 6A shows an embodiment of the invention comprising a hollow tube (e.g. a catheter) housing the base structure. FIG. 9 shows another embodiment of a foldover sensor combined with other components useful in in vivo glucose sensor system embodiments. One illustrative foldover sensor system comprises a processor, a base comprising a first longitudinal member and a second longitudinal member, the first and second longitudinal members each comprising at least one electrode having an electrochemically reactive surface, wherein the electrochemically reactive surface generates an electrochemical signal that is assessed by the processor in the presence of an analyte; and a computer-readable program code having instructions, which when executed cause the processor to assess electrochemical signal data obtained from the electrodes; and compute an analyte presence or concentration based upon the electrochemical signal data obtained from the electrode. In this system, the base of the sensor is folded longitudinally such that the first longitudinal member substantially overlaps the second longitudinal member. Embodiments of the invention described herein can also be adapted and implemented with amperometric sensor structures, for example those disclosed in U.S. Patent Application Publication Nos. 20070227907, 20400025238, 20110319734 and 20110152654, the contents of each of which are incorporated herein by reference.

Illustrative Characteristics of Embodiments of the Invention

The 360° sensor designs that are disclosed herein are designed to address a number of problematical issues that can occur in certain conventional sensor designs. For example, certain continuous glucose monitoring systems involve the use of a single sensor that must be calibrated against a reference value at regular intervals. In such embodiments, system accuracy is dependent upon the output of this individual sensor and may be affected by transient periods of sensor instability. The reliability of such sensor systems can be improved if outputs multiple sensing electrodes are utilized. However, conventional sensor designs that incorporate multiple sensing electrodes typically require additional and costly manufacturing steps. As noted below, embodiments of the invention overcome these problems in this technology.

The simple redundancy provided by embodiments of the invention, namely those that include multiple working electrodes (e.g. those having identical layers of material layers) can be used to address a number of problematical issues that can occur in certain conventional sensor designs. For example, in certain embodiments of the invention, the data obtained from multiple working electrodes can be combined in real-time or during post-processing to enhance sensor reliability. In this context, a number of methods can be used for combining raw outputs from two or more redundant sensors. In one illustrative embodiment, raw values from redundant electrodes are averaged to generate a single output before calculating the final sensor glucose value. In another illustrative embodiment, sensor algorithms can be employed which analyze raw data from individual and multiple working electrodes in order to identify fault conditions (e.g. Electrochemical Impedance Check, noise, drift etc.). In such embodiments, only raw data from the uncompromised electrodes is then used for the final analyte determinations.

Embodiments of the invention are also useful in glucose diagnostic sensing applications. For example, a multi-electrode glucose sensor system can also be used to improve the decisions made by the device algorithm (thus reliability) by providing additional information on the sensing environment. In such embodiments, different electrode layer chemistries are deposited and/or different electrode potentials are applied to different electrodes, for example those that are different from those used for glucose sensing, such as a working electrode run at −650 mV as opposed to 535 mV (which can be instead used only for glucose sensing) in order to characterize factors associated with glucose sensor reliability including background noise, the presence or concentrations of interfering species, oxygen concentrations or the pH of an environment in which a glucose sensor is placed.

Embodiments of the invention are also useful to increase the reliability of glucose sensor measurements in diabetic patient hyperglycemic and/or hypoglycemic blood glucose concentration ranges. For example, in certain embodiments of the invention, individual electrodes can be used to obtain higher accuracy in specific hyperglycemic and/or hypoglycemic regions. In this context, a multi-working electrode sensor can also provide the bandwidth for specific designs that can provide highly reliable data at specific hyperglycemic and/or hypoglycemic ranges. This can be accomplished, for example, by optimizing the electrode sizes or designs. In particular, a smaller working electrode generally shows reduced drift, better linearity and low background. However, the limited signal magnitude with such smaller electrodes can limit sensor accuracy at certain hyperglycemic ranges (high glucose levels). Similarly, a larger working electrode typically shows more noise and higher background at hypoglycemic ranges (low glucose levels). However, such larger electrodes can give a higher dynamic range for hyperglycemic sensitivity. In embodiments of the invention comprising a multi-working electrode system, these two or more electrodes can be combined into a single sensor in order to obtain the optimal hypoglycemic and hyperglycemic range information from each working electrode of a different size.

Embodiments of the invention are also useful to optimize glucose sensor performance based on factors specific to the amount of time after sensor implantation that glucose is sensed. For example, embodiments of the invention can be used to assess the performance and/or increase the reliability of sensors used in early wear (i.e. the first 24 hours or day 1) performance and late wear (e.g. days 7-10) performance by using sensors having working electrodes upon which selective chemistry designed for either early wear performance or late wear performance is disposed. For example, glucose sensors having working electrodes upon which thinner layers of materials are deposited (e.g. glucose oxidase, a glucose limiting membrane etc.) are observed to produce more accurate readings in early wear, but tend to lose sensitivity after day 2. A thinner or high-permeable chemistry may hydrate quickly for improved day 1 accuracy but may not be ideal for long term wear. In contrast, glucose sensors having working electrodes upon which thicker layers of materials (e.g. an analyte sensing layer, an analyte modulating layer etc.) are deposited are observed to exhibit stability and reliability during later wear but not at start-up (early wear). For example, a thicker or low-permeable chemistry may hydrate more slowly compromising day 1 accuracy but provide long-term sensitivity (improved later wear accuracy). Consequently, by selectively controlling the properties of the materials disposed on a working electrode, (e.g. concentrations of reagents, thickness, permeability) one can to optimize sensor performance based on time after implantation. In this context, the multi-electrode systems disclosed herein allow dedicated electrodes to have specialized material layers that are designed to optimize early and/or late wear sensor accuracy.

B. Illustrative Analyte Sensor Constituents Used in

Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Sensors of the invention typically include a base constituent (see, e.g. element 402 in FIG. 12). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of or coated with a wide variety of materials having desirable qualities such as dielectric properties, water impermeability and hermeticity. Some materials include metallic, and/or ceramic and/or polymeric substrates or the like. Embodiments of the invention utilize base substrates formed from flexible material(s) selected for an ability to transition from a first configuration to a second configuration when the base substrate is folded to form a fixed bend. Such materials must be flexible enough to bend but not break when folded. At the same time, such materials must be stiff/rigid enough to form a fixed (permanent) bend when folded.

Conductive Constituent

The electrochemical sensors of the invention typically include a conductive constituent disposed upon the base constituent that includes at least one electrode for contacting an analyte or its byproduct (e.g. oxygen and/or hydrogen peroxide) to be assayed (see, e.g. element 404 in FIG. 12). The term "conductive constituent" is used herein according to art accepted terminology and refers to electrically conductive sensor elements such as electrodes, contact pads, traces and the like. An illustrative example of this is a conductive constituent that forms a working electrode that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 410 or a reaction product of this interaction (e.g. hydrogen peroxide). Illustrative examples of such elements include electrodes which are capable of producing variable detectable signals in the presence of variable concentrations of molecules such as hydrogen peroxide or oxygen.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate. Optionally, the electrodes can be disposed on a single surface or side of the sensor structure. Alternatively, the electrodes can be disposed on a multiple surfaces or sides of the sensor structure. In certain embodiments of the invention, the reactive surfaces of the electrodes are of different relative areas/sizes, for example a 1× reference electrode, a 2.6× working electrode and a 3.6× counter electrode.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic polyurethanes, cellulose acetate (including cellulose acetate incorporating agents such as poly(ethylene glycol), polyethersulfones, polytetra-fluoroethylenes, the perfluoronated ionomer Nafion™, polyphenylenediamine, epoxy and the like.

Analyte Sensing Constituent

The electrochemical sensors of the invention include an analyte sensing constituent disposed on the electrodes of the sensor (see, e.g. element 410 in FIG. 12). The term "analyte sensing constituent" is used herein according to art accepted terminology and refers to a constituent comprising a material that is capable of recognizing or reacting with an analyte whose presence is to be detected by the analyte sensor apparatus. Typically, this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture. The addition of a cross-linking reagent to the protein mixture creates a protein paste. The concentration of the cross-linking reagent to be added may vary according to the concentration of the protein mixture. While glutaraldehyde is an illustrative crosslinking reagent, other cross-linking reagents may also be used or may be used in place of glutaraldehyde. Other suitable cross-linkers also may be used, as will be evident to those skilled in the art.

As noted above, in some embodiments of the invention, the analyte sensing constituent includes an agent (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; Jan. 7, 1991) the entire contents of which are incorporated herein by reference.

Protein Constituent

The electrochemical sensors of the invention optionally include a protein constituent disposed between the analyte sensing constituent and the analyte modulating constituent (see, e.g. element 416 in FIG. 12). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically, the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 414 in FIG. 12). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

Analyte Modulating Constituent

The electrochemical sensors of the invention include an analyte modulating constituent disposed on the sensor (see, e.g. element 412 in FIG. 12). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferants, such as ascorbic acid and uric acid, diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The analyte modulating sensor membrane assembly serves several functions, including selectively allowing the passage of glucose therethrough (see, e.g. U.S. Patent Application No. 2011-0152654).

Cover Constituent

The electrochemical sensors of the invention include one or more cover constituents which are typically electrically insulating protective constituents (see, e.g. element 406 in FIG. 12). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photoimageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Multilayered Sensor Stacks

An embodiment of the invention having a layered stack of constituents is shown in FIG. 12. FIG. 12 illustrates a cross-section of a typical sensor embodiment 400 of the present invention that includes constituents discussed above. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 12. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 12 includes a base substrate layer 402 to support the sensor 400. The base substrate layer 402 can be made of a material such as a metal and/or a ceramic and/or a polymeric substrate, which may be self-supporting or further supported by another material as is known in the art. Embodiments of the invention include a conductive layer 404 which is disposed on and/or combined with the base substrate layer 402. Typically, the conductive layer 404 comprises one or more electrically conductive elements that function as electrodes. An operating sensor 400 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 402 and/or conductive layer 404 can be generated using many known techniques and materials. In certain embodiments of the invention, the electrical circuit of the sensor is defined by etching the disposed conductive layer 404 into a desired pattern of conductive paths. A typical electrical circuit for the sensor 400 comprises two or more adjacent conductive paths with regions at a proximal end to form contact pads and regions at a distal end to form sensor electrodes. An electrically insulating cover layer 406 such as a polymer coating can be disposed on portions of the sensor 400. Acceptable polymer coatings for use as the insulating protective cover layer 406 can include, but are not limited to, non-toxic biocompatible polymers such as silicone compounds, polyimides, biocompatible solder masks, epoxy acrylate copolymers, or the like. In the sensors of the present invention, one or more exposed regions or apertures 408 can be made through the cover layer 406 to open the conductive layer 404 to the external environment and to, for example, allow an analyte such as glucose to permeate the layers of the sensor and be sensed by the sensing elements. Apertures 408 can be formed by a number of techniques, including laser ablation, tape masking, chemical milling or etching or photolithographic development or the like. In certain embodiments of the invention, during manufacture, a secondary photoresist can also be applied to the protective layer 406 to define the regions of the protective layer to be removed to form the aperture(s) 408. The exposed electrodes and/or contact pads can also undergo secondary processing (e.g. through the apertures 408), such as additional plating processing, to prepare the surfaces and/or strengthen the conductive regions.

In the sensor configuration shown in FIG. 12, an analyte sensing layer 410 is disposed on one or more of the exposed electrodes of the conductive layer 404. Typically, the analyte sensing layer 410 is an enzyme layer. Most typically, the analyte sensing layer 410 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 410 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can be monitored by any one of a variety of sensor detector apparatuses such as a universal sensor amperometric biosensor detector or one of the other variety of similar devices known in the art such as glucose monitoring devices produced by Medtronic Diabetes.

In embodiments of the invention, the analyte sensing layer 410 can be applied over portions of the conductive layer or over the entire region of the conductive layer. Typically, the analyte sensing layer 410 is disposed on the working electrode which can be the anode or the cathode. Optionally, the analyte sensing layer 410 is also disposed on a counter and/or reference electrode. Methods for generating a thin analyte sensing layer 410 include brushing the layer onto a substrate (e.g. the reactive surface of a platinum black electrode), as well as spin coating processes, dip and dry processes, low shear spraying processes, ink-jet printing processes, silk screen processes and the like. In certain embodiments of the invention, brushing is used to: (1) allow for a precise localization of the layer; and (2) push the layer deep into the architecture of the reactive surface of an electrode (e.g. platinum black produced by an electrodeposition process).

Typically, the analyte sensing layer 410 is coated and or disposed next to one or more additional layers. Optionally, the one or more additional layers includes a protein layer 416 disposed upon the analyte sensing layer 410. Typically, the protein layer 416 comprises a protein such as human serum albumin, bovine serum albumin or the like. Typically, the protein layer 416 comprises human serum albumin. In some embodiments of the invention, an additional layer includes an analyte modulating layer 412 that is disposed above the analyte sensing layer 410 to regulate analyte contact with the analyte sensing layer 410. For example, the analyte modulating membrane layer 412 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In certain embodiments of the invention, an adhesion promoter layer 414 is disposed between the analyte modulating layer 412 and the analyte sensing layer 410 as shown in FIG. 12 in order to facilitate their contact and/or adhesion. In a specific embodiment of the invention, an adhesion promoter layer 414 is disposed between the analyte modulating layer 412 and the protein layer 416 as shown in FIG. 12 in order to facilitate their contact and/or adhesion. The adhesion promoter layer 414 can be made from any one of a wide variety of materials known in the art to facilitate the bonding between such layers. Typically, the adhesion promoter layer 414 comprises a silane compound. In alternative embodiments, protein or like molecules in the analyte sensing layer 410 can be sufficiently crosslinked or otherwise prepared to allow the analyte modulating membrane layer 412 to be disposed in direct contact with the analyte sensing layer 410 in the absence of an adhesion promoter layer 414.

C. Typical System Embodiments of the Invention

A specific illustrative system embodiment consists of a glucose sensor comprising a folded base architecture as disclosed herein, a transmitter, a recorder and receiver and a glucose meter. In this system, radio signals from the transmitter can be sent to the pump receiver at regular time periods (e.g. every 5 minutes) to provide real-time sensor glucose (SG) values. Values/graphs can be displayed on a monitor of the pump receiver so that a user can self monitor blood glucose and deliver insulin using their own insulin pump. Typically, the sensor systems disclosed herein can communicate with a other medical devices/systems via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically, in such devices, the physiological characteristic values includes a plurality of measurements of blood glucose.

Figure 10:
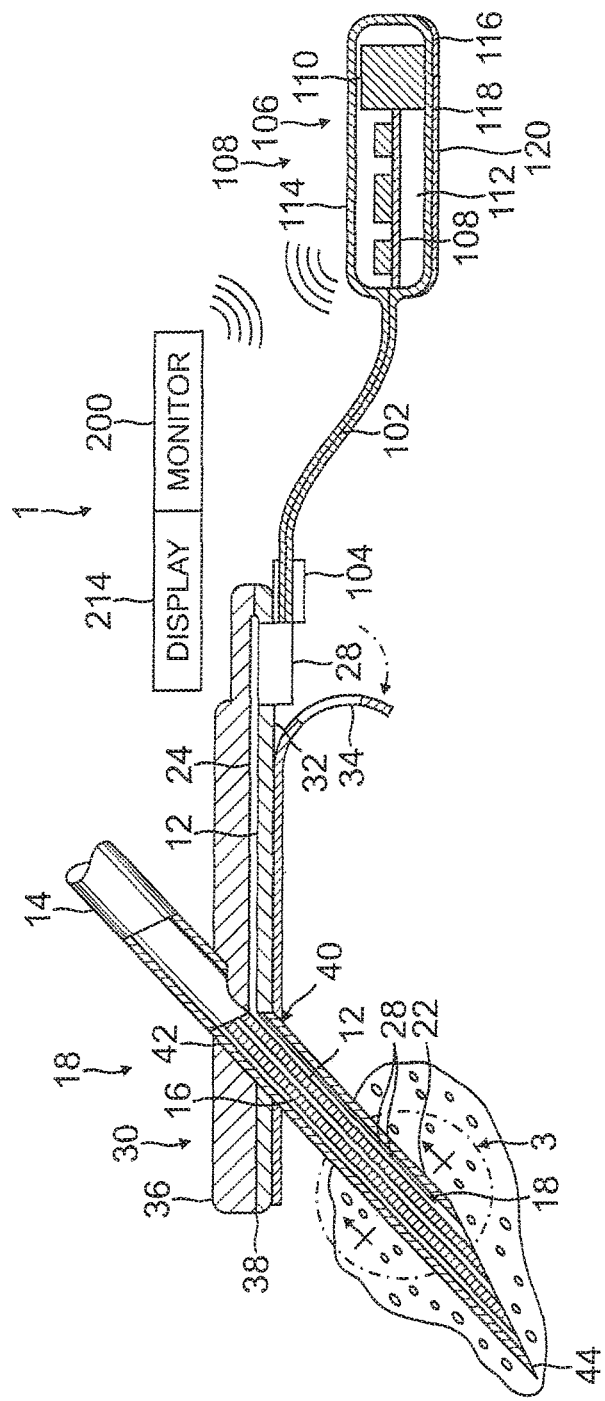
FIG. 10 provides a perspective view illustrating a subcutaneous sensor insertion set, a telemetered characteristic monitor transmitter device, and a data receiving device embodying features of the invention.

FIG. 10 provides a perspective view of one generalized embodiment of subcutaneous sensor insertion system that can be adapted for use with the folded sensor structures disclosed herein and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 10 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The folded base architecture is designed so that the sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 214 for monitoring a user's condition in response to signals derived from the sensor electrodes 20. The connection portion 24 may be conveniently connected electrically to the monitor 200 or a characteristic monitor transmitter 200 by a connector block 28 (or the like) as shown and described in U.S. Pat. No. 5,482,473, entitled FLEX CIRCUIT CONNECTOR, which is incorporated by reference.

As shown in FIG. 10, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 200 is coupled to a sensor set 10 by a cable 402 through a connector 104 that is electrically coupled to the connector block 28 of the connector portion 24 of the sensor set 10.

In the embodiment shown in FIG. 10, the telemetered characteristic monitor 400 includes a housing 106 that supports a printed circuit board 108, batteries 110, antenna 112, and the cable 202 with the connector 104. In some embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In some embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 116 may have an underside surface coated with a suitable pressure sensitive adhesive layer 118, with a peel-off paper strip 120 normally provided to cover and protect the adhesive layer 118, until the sensor set telemetered characteristic monitor transmitter 200 is ready for use.

In the illustrative embodiment shown in FIG. 10, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. No. 4,562,751; 4,678,408; 4,685,903 or 4,573,994, to control delivery of insulin to a diabetic patient.

In the illustrative embodiment shown in FIG. 10, the sensor electrodes 10 may be used in a variety of sensing applications and may be configured in a variety of positions on a folded base structure and further be formed to include materials that allow a wide variety of functions. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 10, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 402 through a connector that is electrically coupled to the connector block 28 of the connection portion 24. In an alternative embodiment, the cable may be omitted. In this embodiment of the invention, the monitor 200 may include an appropriate connector for direct connection to the connection portion 104 of the sensor set 10. The sensor set 10 may be modified to have the connector portion 104 positioned at a different location, e.g., on top of the sensor set to facilitate placement of the monitor 200 over the sensor set.

As noted above, embodiments of the sensor elements and sensors can be operatively coupled to a variety of other system elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Figure 11:
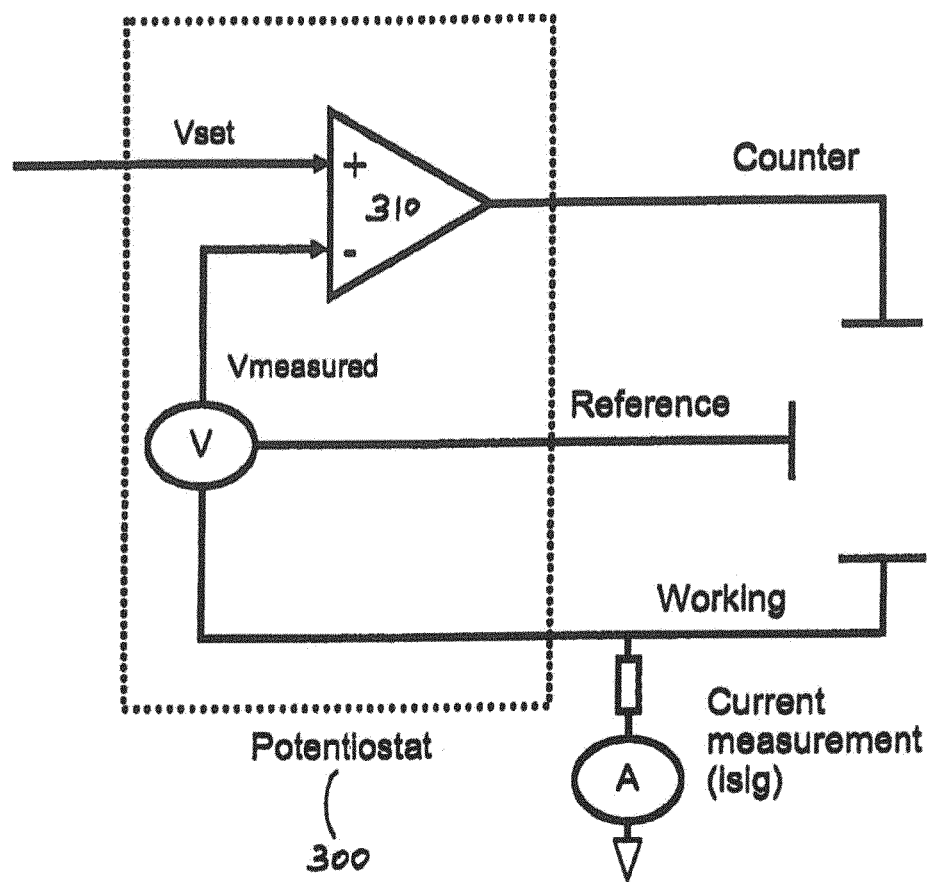
FIG. 11 shows a schematic of a potentiostat that may be used to measure current in embodiments of the present invention.

FIG. 11 shows a schematic of a potentiostat that may be used to measure current in embodiments of the present invention. As shown in FIG. 11, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (Isig) that is output from the potentiostat.

Embodiments of the invention include devices which process display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver every 5 minutes to provide real-time sensor glucose (SG) values. Values/graphs are displayed on a monitor of the pump receiver so that a user can self monitor blood glucose and deliver insulin using their own insulin pump. Typically, an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically, in such devices, the physiological characteristic values include a plurality of measurements of blood glucose.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The descriptions and specific examples, while indicating some embodiments of the present invention are given by way of illustration and not limitation. Many changes and modifications within the scope of the present invention may be made without departing from the spirit thereof, and the invention includes all such modifications.

The invention claimed is:

1. A method of sensing an analyte within a mammal comprising:
   (a) implanting an analyte sensor apparatus within the mammal, the analyte sensor apparatus comprising:
   a base substrate comprising a planar sheet of a flexible material adapted to transition from a first configuration to a second configuration when the base substrate is folded to form a fixed bend;
   a working electrode, a counter electrode and a reference electrode disposed upon a first surface of the base substrate;
   a plurality of contact pads disposed upon the first surface of the base substrate;

a plurality of electrical conduits disposed upon the first surface of the base substrate, wherein the plurality of electrical conduits are adapted to transmit electrical signals between the working electrode, the counter electrode or the reference electrode and the plurality of contact pads separated by the fixed bend;

an analyte sensing layer comprising glucose oxidase disposed over the working electrode, wherein the analyte sensing layer detectably alters the electrical current at the working electrode in the presence of an analyte; and an analyte modulating layer disposed over the analyte sensing layer, wherein the analyte modulating layer modulates the diffusion of analyte therethrough;

wherein:
the base substrate comprises the fixed bend so as to form a configuration characterized in that:
at least one working electrode, counter electrode or reference electrode is disposed on a first side of the fixed bend; and
at least one working electrode, counter electrode or reference electrode is disposed on a second side of the fixed bend;
(b) sensing an alteration in current at the working electrode in the presence of the analyte; and
(c) correlating the alteration in current with the presence of the analyte, so that the analyte is sensed.

2. The method of claim 1, wherein the fixed bend configures the base substrate in an orientation such that at least one electrode on the first side of the fixed bend and at least one electrode on the second side of the fixed bend face opposite directions.

3. The method of claim 1, wherein the base substrate comprises at least one of: a demarcation, a perforation, or a kiss cut disposed in an area at which the base substrate is folded.

4. The method of claim 1, wherein:
the analyte sensor apparatus does not comprise a housing that surrounds the analyte sensor apparatus; or
the base substrate does not comprise an electrical via.

5. The method of claim 2, wherein the analyte sensor apparatus further comprises:
a processor;
a computer-readable program code having instructions, which when executed cause the processor to:
assess electrochemical signal data obtained from the working electrode; and
compute analyte concentrations based upon the electrochemical signal data obtained from the working electrode.

6. The method of claim 1, wherein the analyte is glucose.

7. The method of claim 1, wherein the analyte sensor apparatus is implanted within the interstitial space of a diabetic.

8. A method of sensing an analyte within a diabetic patient comprising:
(a) implanting an analyte sensor apparatus within an interstitial space of the diabetic patient, the analyte sensor apparatus comprising:
a base substrate comprising a planar sheet of a flexible material adapted to transition from a first configuration to a second configuration when the base substrate is folded to form a fixed bend;
a working electrode, a counter electrode and a reference electrode disposed upon a first surface of the base substrate;
a plurality of contact pads disposed upon the first surface of the base substrate;
a plurality of electrical conduits disposed upon the first surface of the base substrate, wherein the plurality of electrical conduits are adapted to transmit electrical signals between the working electrode, the counter electrode or the reference electrode and the plurality of contact pads separated by the fixed bend;
an analyte sensing layer comprising glucose oxidase disposed over the working electrode, wherein the analyte sensing layer detectably alters the electrical current at the working electrode in the presence of an analyte; and
an analyte modulating layer disposed over the analyte sensing layer, wherein the analyte modulating layer modulates the diffusion of analyte therethrough;

wherein:
the base substrate comprises the fixed bend so as to form a configuration characterized in that:
at least one working electrode, counter electrode or reference electrode is disposed on a first side of the fixed bend; and
at least one working electrode, counter electrode or reference electrode is disposed on a second side of the fixed bend;
(b) sensing an alteration in current at the working electrode in the presence of the analyte; and
(c) correlating the alteration in current with the presence of the analyte, so that the analyte is sensed.

9. The method of claim 8, wherein the fixed bend configures the base substrate in an orientation such that the working electrode on the first side of the fixed bend and the counter electrode on the second side of the fixed bend face opposite directions.

10. The method of claim 8, wherein the base substrate comprises at least one of: a demarcation, a perforation, or a kiss cut disposed in an area at which the base substrate is folded.

11. The method of claim 8, wherein the base substrate comprises:
a rectangular body;
a first longitudinal arm extending outward from the rectangular body; and
a second longitudinal arm extending outward from the rectangular body; wherein the first longitudinal arm and the second longitudinal arm are parallel to each other.

12. The method of claim 11, further comprising a locking member disposed on the base substrate and adapted to inhibit movement of the first longitudinal arm or the second longitudinal arm.

13. The method of claim 8, wherein:
the analyte sensor apparatus does not comprise a housing that surrounds the analyte sensor apparatus; or
the base substrate does not comprise an electrical via.

14. The method of claim 8, wherein the analyte sensor apparatus further comprises:
a processor;
a computer-readable program code having instructions, which when executed cause the processor to:
assess electrochemical signal data obtained from the working electrode; and
compute analyte concentrations based upon the electrochemical signal data obtained from the working electrode.

15. The method of claim 8, wherein the analyte is glucose.

16. The method of claim 8, wherein the analyte sensing layer comprises glucose oxidase.

* * * * *